United States Patent
Kawabe et al.

(10) Patent No.: US 12,239,714 B2
(45) Date of Patent: Mar. 4, 2025

(54) PHOSPHATIDYLSERINE-BINDING CONJUGATES

(71) Applicant: CANBAS CO., LTD., Numazu (JP)

(72) Inventors: Takumi Kawabe, Numazu (JP); Takuji Sato, Numazu (JP); Tatsuya Kibe, Numazu (JP); Toshiyuki Hibino, Numazu (JP); Jonathan M. Friedman, Numazu (JP); Sayaka Yamamoto, Numazu (JP); Chikako Suda, Numazu (JP)

(73) Assignee: CANBAS CO., LTD., Numazu (JP)

( * ) Notice: Subject to any disclaimer, the term of this patent is extended or adjusted under 35 U.S.C. 154(b) by 98 days.

(21) Appl. No.: 18/090,259

(22) Filed: Dec. 28, 2022

(65) Prior Publication Data
US 2023/0270869 A1    Aug. 31, 2023

Related U.S. Application Data

(60) Provisional application No. 63/295,462, filed on Dec. 30, 2021.

(51) Int. Cl.
| | | |
|---|---|---|
| *A61K 47/64* | (2017.01) | |
| *A61K 31/165* | (2006.01) | |
| *A61K 33/243* | (2019.01) | |
| *A61K 39/395* | (2006.01) | |
| *A61P 35/00* | (2006.01) | |

(52) U.S. Cl.
CPC ............ *A61K 47/64* (2017.08); *A61K 31/165* (2013.01); *A61K 33/243* (2019.01); *A61K 39/3955* (2013.01); *A61P 35/00* (2018.01)

(58) Field of Classification Search
None
See application file for complete search history.

(56) References Cited

FOREIGN PATENT DOCUMENTS

| | | |
|---|---|---|
| EP | 3730152 A1 | 10/2020 |
| WO | 2017/069291 A1 | 4/2017 |

OTHER PUBLICATIONS

Caberoy et al. "Efficient Identification of Phosphatidylserine-Binding Proteins by ORF Phage Display" Biochem Biophys Res Commun. 386:197-201. (Year: 2009).*
Conesa-Zamora et al. "Identification of Phosphatidylserine Binding Site in the C2 Domain that is Important for PKCa Activation and in Vivo Cell Localization" Biochemistry 40:13898-13905. (Year: 2001).*
Kornilov et al. "The architecture of transmembrane and cytoplasmic juxtamembrane regions of Toll-like receptors" Nature Communications 14:1503 (Year: 2023).*
Reddy Chichili et al., "Linkers in the structural biology of protein-protein interactions", Protein Science, Feb. 2013, pp. 153-167, vol. 22(2).
Berge et al., "Pharmaceutical Salts", Journal of Pharmaceutical Science, Jan. 1977, pp. 1-19, vol. 66(1).
Marin-Acevedo et al., "Next generation of immune checkpoint inhibitors and beyond", Journal of Hematology & Oncology, 2021, pp. 1-29, vol. 14(45).
Waldman et al., "A guide to cancer immunotherapy: from T cell basic science to clinical practice", Nature Reviews Immunology, Nov. 2020, pp. 651-668, vol. 20.
Pahlavanneshan et al., "Toll-Like Receptor-Based Strategies for Cancer Immunotherapy", Journal of Immunology Research, May 22, 2021, pp. 1-14, vol. 2021.
Keshavarc et al., "Toll-like receptors (TLRs) in cancer; with an extensive focus on TLR agonists and antagonists" JUBMB Life, 2021, pp. 10-25, vol. 73.
Gadd et al., "Targeted Activation of Toll-Like Receptors: Conjugation of a Toll-Like Receptor 7 Agonist to a Monoclonal Antibody Maintains Antigen Binding and Specificity", Bioconjugate Chem., Jul. 1, 2015, pp. 1743-1752, vol. 26(8).
Ackerman et al., "Immune-stimulating antibody conjugates elicit robust myeloid activation and durable anti-tumor Immunity", National Cancer, Jan. 2021, pp. 18-33, vol. 2(1).
Thurber et al., "Antibody tumor penetration: Transport opposed by systemic and antigen-mediated clearance", Adv Drug Deliv Rev, Sep. 2008, pp. 1-32, vol. 60(12).
Chang et al., "Targeting phosphatidylserine for Cancer therapy: prospects and challenges", Theranostics, Jul. 23, 2020, pp. 9214-9229, vol. 10(20).
Kapty et al., "Evaluation of Phosphatidylserine-Binding Peptides Targeting Apoptotic Cells", Journal of Biomolecular Screening, Dec. 2012, pp. 1293-1301, vol. 17(10).
Igarashi et al., "A Novel Phosphatidylserine-binding Peptide Motif Defined by an Anti-idiotypic Monoclonal Antibody", The Journal of Biological Chemistry, Dec. 8, 1995, pp. 29075-29078, vol. 270(49).
Laumonier et al., "A New Peptidic Vector for Molecular Imaging of Apoptosis, Identified by Phage Display Technology", Journal of Biomolecular Screening, Aug. 2006, pp. 437-545, vol. 11(5).
Thapa et al., "Discovery of a phosphatidylserine-recognizing peptide and its utility in molecular imaging of tumour apoptosis", Journal of Cellular and Molecular Medicine, Sep. 2008, pp. 1649-1660, vol. 12(5A).
Sha et al., "Cell cycle phenotype-based optimization of G2-abrogating peptides yields CBP501 with a unique mechanism of action at the G2 checkpoint", Molecular Cancer Therapeutics, Jan. 1, 2007, pp. 147-153, vol. 6(1).
Mine et al., "CBP501-Calmodulin Binding Contributes to Sensitizing Tumor Cells to Cisplatin and Bleomycin", Molecular Cancer Therapeutics, Oct. 1, 2011, pp. 1929-1938, vol. 10(10).

(Continued)

*Primary Examiner* — Sudhakar Katakam
*Assistant Examiner* — Zachary J Miknis
(74) *Attorney, Agent, or Firm* — Pillsbury Winthrop Shaw Pittman, LLP (CV)

(57) ABSTRACT

Presented herein, in certain aspects, are conjugates capable of binding phosphatidylserine (PS) and toll-like receptors (TLRs), and their uses for the treatment of selected diseases and disorders, such as cancer.

22 Claims, 8 Drawing Sheets
Specification includes a Sequence Listing.

(56) References Cited

OTHER PUBLICATIONS

Sakakibara et al., "CBP501 induces immunogenic tumor cell death and CD8 T cell infiltration into tumors in combination with platinum, and increases the efficacy of immune checkpoint inhibitors against tumors in mice", Oncotarget, Sep. 16, 2017, pp. 78277-78288, vol. 8(45).
Mine et al., "CBP501 suppresses macrophage induced cancer stem cell like features and metastases", Oncotarget, Jul. 17, 2017, pp. 64015-64031, vol. 8(38).
Barth et al., "A fluorogenic cyclic peptide for imaging and quantification of drug-induced apoptosis", Nature Communications, 2020, pp. 1-14, vol. 11(4027).
Patent Cooperation Treaty, International Search Report and Written Opinion issued in PCT/IB2022/062902, Mar. 27, 2023, pp. 1-18.
Gong et al., "5379: Anti-Tumor Responses by Ibrutinib and Anti-PD-1 Blockade Is Enhanced by Phosphatidylserine-Targeting Antibody Therapy", Blood, Dec. 2, 2016 pp. 1-2, vol. 128(22).
Freimark et al., "Antibody-Mediated Phosphatidylserine Blockade Enhances the Antitumor Responses to CTLA-4 and PD-1 Antibodies in Melanoma", Cancer Immunology Research, Apr. 4, 2016, pp. 531-540, vol. 4(6).
Gray et al., "Phosphatidylserine-targeting antibodies augment the anti-tumorigenic activity of anti-PD-1 therapy by enhancing immune activation and downregulating pro-oncogenic factors induced by T-cell checkpoint inhibition in murine triple-negative breast cancers", Breast Cancer Research, Dec. 2016, pp. 1-14, vol. 18(1).
Giese et al., "Abstract 2767: Phosphatidylserine targeting and radiation improves survival in a mouse tumor model resistant to checkpoint blockade", Cancer Research, Jul. 1, 2018, p. 2767, vol. 78(13).
Hilbert et al. "Synergistic Stimulation with Different TLR7 Ligands Modulates Gene Expression Patterns in the Human Plasmacytoid Dendritic Cell Line CAL-1", Mediators of Inflammation, 2015, pp. 1-13, vol. 2015 (948540).
Janovec et al., "Toll-like receptor dual-acting agonists are potent inducers of PBMC-produced cytokines that inhibit hepatitis B virus production in primary human hepatocytes", Scientific Reports, Jul. 29, 2020, pp. 1-11, vol. 10(1).
Butterfield et al., "TLR9-Activating CpG-B ODN but Not TLR7 Agonists Triggers Antibody Formation to Factor IX in Muscle Gene Transfer", Human Gene Therapy Methods, Jun. 2019, pp. 81-92, vol. 30(3).
Patent Cooperation Treaty, International Preliminary Report on Patentability issued in PCT/IB2022/062902, Jun. 20, 2024, pp. 1-10.

\* cited by examiner

Distribution of the Cy5.5 version of TSA006 (TSA013) in balb/c mouse.

SEQUENCE LISTING

```
Sequence total quantity: 43
SEQ ID NO: 1                  moltype = AA  length = 6
FEATURE                       Location/Qualifiers
source                        1..6
                              mol_type = protein
                              organism = synthetic construct
SEQUENCE: 1
LIKKPF                                                                           6

SEQ ID NO: 2                  moltype = AA  length = 6
FEATURE                       Location/Qualifiers
source                        1..6
                              mol_type = protein
                              organism = synthetic construct
SEQUENCE: 2
PGDLSR                                                                           6

SEQ ID NO: 3                  moltype = AA  length = 7
FEATURE                       Location/Qualifiers
source                        1..7
                              mol_type = protein
                              organism = synthetic construct
SEQUENCE: 3
CLIKKPF                                                                          7

SEQ ID NO: 4                  moltype = AA  length = 7
FEATURE                       Location/Qualifiers
source                        1..7
                              mol_type = protein
                              organism = synthetic construct
SEQUENCE: 4
CPGDLSR                                                                          7

SEQ ID NO: 5                  moltype = AA  length = 14
FEATURE                       Location/Qualifiers
source                        1..14
                              mol_type = protein
                              organism = synthetic construct
SEQUENCE: 5
FNFRLKAGAK IRFG                                                                 14

SEQ ID NO: 6                  moltype = AA  length = 12
FEATURE                       Location/Qualifiers
source                        1..12
                              mol_type = protein
                              organism = synthetic construct
VARIANT                       2
                              note = X can be any amino acid
VARIANT                       4
                              note = X can be any amino acid
VARIANT                       7..9
                              note = X can be any amino acid
VARIANT                       11
                              note = X can be any amino acid
SEQUENCE: 6
FXFXLKXXXK XR                                                                   12

SEQ ID NO: 7                  moltype = AA  length = 6
FEATURE                       Location/Qualifiers
source                        1..6
                              mol_type = protein
                              organism = synthetic construct
SEQUENCE: 7
TLVSSL                                                                           6

SEQ ID NO: 8                  moltype = AA  length = 9
FEATURE                       Location/Qualifiers
source                        1..9
                              mol_type = protein
                              organism = synthetic construct
SEQUENCE: 8
CLSYYPSYC                                                                        9

SEQ ID NO: 9                  moltype = AA  length = 7
FEATURE                       Location/Qualifiers
source                        1..7
                              mol_type = protein
                              organism = synthetic construct
```

```
SITE                    7
                        note = D-Arginine
SEQUENCE: 9
GEGKGGR                                                                 7

SEQ ID NO: 10           moltype = AA  length = 7
FEATURE                 Location/Qualifiers
source                  1..7
                        mol_type = protein
                        organism = synthetic construct
SITE                    1
                        note = D-Glycine
SITE                    3
                        note = D-Glycine
SITE                    5..6
                        note = D-Glycine
SITE                    2
                        note = D-Glutamic acid
SITE                    4
                        note = D-Lysine
SITE                    7
                        note = D-Arginine
SEQUENCE: 10
GEGKGGR                                                                 7

SEQ ID NO: 11           moltype = AA  length = 4
FEATURE                 Location/Qualifiers
source                  1..4
                        mol_type = protein
                        organism = synthetic construct
SITE                    4
                        note = D-Arginine
SEQUENCE: 11
GEGR                                                                    4

SEQ ID NO: 12           moltype = AA  length = 4
FEATURE                 Location/Qualifiers
source                  1..4
                        mol_type = protein
                        organism = synthetic construct
SITE                    4
                        note = D-Arginine
SITE                    1
                        note = D-Glycine
SITE                    3
                        note = D-Glycine
SITE                    2
                        note = Glutamic acid
SEQUENCE: 12
GEGR                                                                    4

SEQ ID NO: 13           moltype = AA  length = 5
FEATURE                 Location/Qualifiers
source                  1..5
                        mol_type = protein
                        organism = synthetic construct
SEQUENCE: 13
RGEGR                                                                   5

SEQ ID NO: 14           moltype = AA  length = 5
FEATURE                 Location/Qualifiers
source                  1..5
                        mol_type = protein
                        organism = synthetic construct
SITE                    3
                        note = D-Glutamic acid
SITE                    1
                        note = D-Arginine
SITE                    5
                        note = D-Arginine
SITE                    2
                        note = D-Glycine
SITE                    4
                        note = D-Glycine
SEQUENCE: 14
RGEGR                                                                   5

SEQ ID NO: 15           moltype = AA  length = 7
FEATURE                 Location/Qualifiers
```

| | | |
|---|---|---|
| source | 1..7<br>mol_type = protein<br>organism = synthetic construct | |
| REGION | 1..7<br>note = Peptide is circular | |
| SEQUENCE: 15 | | |
| RKKWFGC | | 7 |
| | | |
| SEQ ID NO: 16<br>FEATURE<br>source | moltype = AA   length = 12<br>Location/Qualifiers<br>1..12<br>mol_type = protein<br>organism = synthetic construct | |
| SITE | 1<br>note = D-Bpa | |
| SITE | 2<br>note = D-Serine | |
| SITE | 4<br>note = D-Serine | |
| SITE | 3<br>note = D-Tryptophan | |
| SITE | 5<br>note = D-Phe-2,3,4,5,6-F | |
| SITE | 6<br>note = D-Cha | |
| SITE | 7..9<br>note = D-Arginine | |
| SITE | 10<br>note = D-Glutamine | |
| SITE | 11..12<br>note = D-Arginine | |
| SEQUENCE: 16 | | |
| XSWSXXRRRQ RR | | 12 |
| | | |
| SEQ ID NO: 17<br>FEATURE<br>source | moltype = AA   length = 12<br>Location/Qualifiers<br>1..12<br>mol_type = protein<br>organism = synthetic construct | |
| SITE | 1..3<br>note = D-Arginine | |
| SITE | 4<br>note = D-Glutamine | |
| SITE | 5..6<br>note = D-Arginine | |
| SITE | 7<br>note = D-Bpa | |
| SITE | 8<br>note = D-Serine | |
| SITE | 10<br>note = D-Serine | |
| SITE | 9<br>note = D-Tryptophan | |
| SITE | 11<br>note = D-Phe-2,3,4,5,6-F | |
| SITE | 12<br>note = D-Cha | |
| SEQUENCE: 17 | | |
| RRRQRRXSWS XX | | 12 |
| | | |
| SEQ ID NO: 18<br>FEATURE<br>source | moltype = AA   length = 12<br>Location/Qualifiers<br>1..12<br>mol_type = protein<br>organism = synthetic construct | |
| SITE | 1<br>note = D-Bpa | |
| SITE | 2<br>note = D-Serine | |
| SITE | 4<br>note = D-Serine | |
| SITE | 3<br>note = D-Tryptophan | |
| SITE | 5<br>note = D-Phe-2,3,4,5,6-F | |
| SITE | 6<br>note = D-Cha | |
| SITE | 7..8<br>note = D-Arginine | |

```
SITE                    10..12
                        note = D-Arginine
SITE                    9
                        note = D-Glutamine
SEQUENCE: 18
XSWSXXRRQR RR                                                                    12

SEQ ID NO: 19           moltype = AA  length = 12
FEATURE                 Location/Qualifiers
source                  1..12
                        mol_type = protein
                        organism = synthetic construct
SITE                    1..2
                        note = D-Arginine
SITE                    4..6
                        note = D-Arginine
SITE                    3
                        note = D-Glutamine
SITE                    7
                        note = D-Bpa
SITE                    8
                        note = D-Serine
SITE                    10
                        note = D-Serine
SITE                    9
                        note = D-Tryptophan
SITE                    11
                        note = D-Phe-2,3,4,5,6-F
SITE                    12
                        note = D-Cha
SEQUENCE: 19
RRQRRRXSWS XX                                                                    12

SEQ ID NO: 20           moltype = AA  length = 12
FEATURE                 Location/Qualifiers
source                  1..12
                        mol_type = protein
                        organism = synthetic construct
SITE                    1
                        note = D-Cha
SITE                    2
                        note = D-Phe-2,3,4,5,6-F
SITE                    3
                        note = D- Serine
SITE                    5
                        note = D- Serine
SITE                    4
                        note = D-Tryptophan
SITE                    6
                        note = D-Bpa
SITE                    7..9
                        note = D-Arginine
SITE                    10
                        note = D-Glutamine
SITE                    11..12
                        note = D-Arginine
SEQUENCE: 20
XXSWSXRRRQ RR                                                                    12

SEQ ID NO: 21           moltype = AA  length = 12
FEATURE                 Location/Qualifiers
source                  1..12
                        mol_type = protein
                        organism = synthetic construct
SITE                    1..3
                        note = D-Arginine
SITE                    5..6
                        note = D-Arginine
SITE                    4
                        note = D-Glutamine
SITE                    7
                        note = D-Cha
SITE                    8
                        note = D-Phe-2,3,4,5,6-F
SITE                    9
                        note = D-Serine
SITE                    11
                        note = D-Serine
SITE                    10
```

```
                         note = D-Tryptophan
SITE                     12
                         note = D-Bpa
SEQUENCE: 21
RRRQRRXXSW SX                                                                      12

SEQ ID NO: 22            moltype = AA  length = 12
FEATURE                  Location/Qualifiers
source                   1..12
                         mol_type = protein
                         organism = synthetic construct
SITE                     1
                         note = D-Cha
SITE                     2
                         note = D-Phe-2,3,4,5,6-F
SITE                     3
                         note = D-Serine
SITE                     5
                         note = D-Serine
SITE                     4
                         note = D-Tryptophan
SITE                     6
                         note = D-Bpa
SITE                     7..8
                         note = D-Arginine
SITE                     10..12
                         note = D-Arginine
SITE                     9
                         note = D-Glutamine
SEQUENCE: 22
XXSWSXRRQR RR                                                                      12

SEQ ID NO: 23            moltype = AA  length = 12
FEATURE                  Location/Qualifiers
source                   1..12
                         mol_type = protein
                         organism = synthetic construct
SITE                     1..2
                         note = D-Arginine
SITE                     4..6
                         note = D-Arginine
SITE                     3
                         note = D-Glutamine
SITE                     7
                         note = D-Cha
SITE                     8
                         note = D-Phe-2,3,4,5,6-F
SITE                     9
                         note = D-Serine
SITE                     11
                         note = D-Serine
SITE                     10
                         note = D-Tryptophan
SITE                     12
                         note = D-Bpa
SEQUENCE: 23
RRQRRRXXSW SX                                                                      12

SEQ ID NO: 24            moltype = AA  length = 12
FEATURE                  Location/Qualifiers
source                   1..12
                         mol_type = protein
                         organism = synthetic construct
SITE                     1..6
                         note = D-Arginine
SITE                     7
                         note = D-Cha
SITE                     8
                         note = D-Phe-2,3,4,5,6-F
SITE                     9
                         note = D-Serine
SITE                     11
                         note = D-Serine
SITE                     10
                         note = D-Tryptophan
SITE                     12
                         note = D-Bpa
SEQUENCE: 24
RRRRRRXXSW SX                                                                      12
```

```
SEQ ID NO: 25          moltype = AA   length = 12
FEATURE                Location/Qualifiers
source                 1..12
                       mol_type = protein
                       organism = synthetic construct
SITE                   1
                       note = D-Cha
SITE                   2
                       note = D-Phe-2,3,4,5,6-F
SITE                   3
                       note = D-Serine
SITE                   5
                       note = D-Serine
SITE                   4
                       note = D-Tryptophan
SITE                   6
                       note = D-Bpa
SITE                   7..12
                       note = D-Arginine
SEQUENCE: 25
XXSWSXRRRR RR                                                              12

SEQ ID NO: 26          moltype = AA   length = 12
FEATURE                Location/Qualifiers
source                 1..12
                       mol_type = protein
                       organism = synthetic construct
SITE                   1..6
                       note = D-Arginine
SITE                   7
                       note = D-Bpa
SITE                   8
                       note = D-Serine
SITE                   10
                       note = D-Serine
SITE                   9
                       note = D-Tryptophan
SITE                   11
                       note = D-Phe-2,3,4,5,6-F
SITE                   12
                       note = D-Cha
SEQUENCE: 26
RRRRRRXSWS XX                                                              12

SEQ ID NO: 27          moltype = AA   length = 12
FEATURE                Location/Qualifiers
source                 1..12
                       mol_type = protein
                       organism = synthetic construct
SITE                   1
                       note = D-Bpa
SITE                   2
                       note = D-Serine
SITE                   4
                       note = D-Serine
SITE                   3
                       note = D-Tryptophan
SITE                   5
                       note = D-Phe-2,3,4,5,6-F
SITE                   6
                       note = D-Cha
SITE                   7..12
                       note = D-Arginine
SEQUENCE: 27
XSWSXXRRRR RR                                                              12

SEQ ID NO: 28          moltype = AA   length = 8
FEATURE                Location/Qualifiers
source                 1..8
                       mol_type = protein
                       organism = synthetic construct
SITE                   1..2
                       note = D-Arginine
SITE                   4..6
                       note = D-Arginine
SITE                   3
                       note = D-Bpa
SITE                   7
```

|  |  |  |
|---|---|---|
| SITE | 8 | |
| | note = D-Cha | |
| SEQUENCE: 28 | | |
| RRXRRRXX | | 8 |
| | | |
| SEQ ID NO: 29 | moltype = AA   length = 8 | |
| FEATURE | Location/Qualifiers | |
| source | 1..8 | |
| | mol_type = protein | |
| | organism = synthetic construct | |
| SITE | 1 | |
| | note = D-Cha | |
| SITE | 2 | |
| | note = D-Phe-2,3,4,5,6-F | |
| SITE | 3..5 | |
| | note = D-Arginine | |
| SITE | 7..8 | |
| | note = D-Arginine | |
| SITE | 6 | |
| | note = D-Bpa | |
| SEQUENCE: 29 | | |
| XXRRRXRR | | 8 |
| | | |
| SEQ ID NO: 30 | moltype = AA   length = 9 | |
| FEATURE | Location/Qualifiers | |
| source | 1..9 | |
| | mol_type = protein | |
| | organism = synthetic construct | |
| SITE | 4 | |
| | note = D-Bpa | |
| SITE | 1..3 | |
| | note = D-Arginine | |
| SITE | 5 | |
| | note = D-Arginine | |
| SITE | 7 | |
| | note = D-Arginine | |
| SITE | 6 | |
| | note = D-Tryptophan | |
| SITE | 8 | |
| | note = D-Phe-2,3,4,5,6-F | |
| SITE | 9 | |
| | note = D-Cha | |
| SEQUENCE: 30 | | |
| RRRXRWRXX | | 9 |
| | | |
| SEQ ID NO: 31 | moltype = AA   length = 9 | |
| FEATURE | Location/Qualifiers | |
| source | 1..9 | |
| | mol_type = protein | |
| | organism = synthetic construct | |
| SITE | 1 | |
| | note = D-Cha | |
| SITE | 2 | |
| | note = D-Phe-2,3,4,5,6-F | |
| SITE | 3 | |
| | note = D-Arginine | |
| SITE | 5 | |
| | note = D-Arginine | |
| SITE | 7..9 | |
| | note = D-Arginine | |
| SITE | 4 | |
| | note = D-Tryptophan | |
| SITE | 6 | |
| | note = D-Bpa | |
| SEQUENCE: 31 | | |
| XXRWRXRRR | | 9 |
| | | |
| SEQ ID NO: 32 | moltype = AA   length = 10 | |
| FEATURE | Location/Qualifiers | |
| source | 1..10 | |
| | mol_type = protein | |
| | organism = synthetic construct | |
| SITE | 5 | |
| | note = D-Bpa | |
| SITE | 1..4 | |
| | note = D-Arginine | |
| SITE | 6 | |
| | note = D-Arginine | |

| | | |
|---|---|---|
| SITE | 8 | |
| | note = D-Arginine | |
| SITE | 7 | |
| | note = D-Tryptophan | |
| SITE | 9 | |
| | note = D-Phe-2,3,4,5,6-F | |
| SITE | 10 | |
| | note = D-Cha | |
| SEQUENCE: 32 | | |
| RRRRXRWRXX | | 10 |
| | | |
| SEQ ID NO: 33 | moltype = AA  length = 10 | |
| FEATURE | Location/Qualifiers | |
| source | 1..10 | |
| | mol_type = protein | |
| | organism = synthetic construct | |
| SITE | 1 | |
| | note = D-Cha | |
| SITE | 2 | |
| | note = D-Phe-2,3,4,5,6-F | |
| SITE | 3 | |
| | note = D-Arginine | |
| SITE | 5 | |
| | note = D-Arginine | |
| SITE | 7..10 | |
| | note = D-Arginine | |
| SITE | 4 | |
| | note = D-Tryptophan | |
| SITE | 6 | |
| | note = D-Bpa | |
| SEQUENCE: 33 | | |
| XXRWRXRRRR | | 10 |
| | | |
| SEQ ID NO: 34 | moltype = AA  length = 9 | |
| FEATURE | Location/Qualifiers | |
| source | 1..9 | |
| | mol_type = protein | |
| | organism = synthetic construct | |
| SITE | 4 | |
| | note = D-Bpa | |
| SITE | 1..3 | |
| | note = D-Arginine | |
| SITE | 5..7 | |
| | note = D-Arginine | |
| SITE | 8 | |
| | note = D-Phe-2,3,4,5,6-F | |
| SITE | 9 | |
| | note = D-Cha | |
| SEQUENCE: 34 | | |
| RRRXRRRXX | | 9 |
| | | |
| SEQ ID NO: 35 | moltype = AA  length = 9 | |
| FEATURE | Location/Qualifiers | |
| source | 1..9 | |
| | mol_type = protein | |
| | organism = synthetic construct | |
| SITE | 1 | |
| | note = D-Cha | |
| SITE | 2 | |
| | note = D-Phe-2,3,4,5,6-F | |
| SITE | 3..5 | |
| | note = D-Arginine | |
| SITE | 7..9 | |
| | note = D-Arginine | |
| SITE | 6 | |
| | note = D-Bpa | |
| SEQUENCE: 35 | | |
| XXRRRXRRR | | 9 |
| | | |
| SEQ ID NO: 36 | moltype = AA  length = 32 | |
| FEATURE | Location/Qualifiers | |
| source | 1..32 | |
| | mol_type = protein | |
| | organism = synthetic construct | |
| SITE | 7 | |
| | note = D-Arginine | |
| SITE | 14 | |
| | note = D-Arginine | |
| SITE | 21 | |

```
                        note = D-Arginine
SITE                    28
                        note = D-Arginine
SEQUENCE: 36
GEGKGGRGEG KGGRGEGKGG RGEGKGGRKK KC                              32

SEQ ID NO: 37           moltype = AA  length = 24
FEATURE                 Location/Qualifiers
source                  1..24
                        mol_type = protein
                        organism = synthetic construct
SEQUENCE: 37
RGEGRRGEGR RGEGRRGEGR KKKC                                       24

SEQ ID NO: 38           moltype = AA  length = 9
FEATURE                 Location/Qualifiers
source                  1..9
                        mol_type = protein
                        organism = synthetic construct
SITE                    1..3
                        note = D-Arginine
SITE                    4
                        note = D-Leucine
SITE                    5..6
                        note = D-Serine
SITE                    7
                        note = D- Valine
SITE                    8
                        note = D-Leucine
SITE                    9
                        note = D-Threonine
SEQUENCE: 38
RRRLSSVLT                                                         9

SEQ ID NO: 39           moltype = AA  length = 32
FEATURE                 Location/Qualifiers
source                  1..32
                        mol_type = protein
                        organism = synthetic construct
SITE                    7
                        note = D-Arginine
SITE                    14
                        note = D-Arginine
SITE                    21
                        note = D-Arginine
SITE                    28
                        note = D-Arginine
SEQUENCE: 39
TLVSSLRTLV SSLRTLVSSL RTLVSSLRKK KC                              32

SEQ ID NO: 40           moltype = AA  length = 64
FEATURE                 Location/Qualifiers
source                  1..64
                        mol_type = protein
                        organism = synthetic construct
SITE                    7
                        note = D-Arginine
SITE                    14
                        note = D-Arginine
SITE                    21
                        note = D-Arginine
SITE                    28
                        note = D-Arginine
SITE                    35
                        note = D-Arginine
SITE                    42
                        note = D-Arginine
SITE                    49
                        note = D-Arginine
SITE                    56
                        note = D-Arginine
SEQUENCE: 40
TLVSSLRTLV SSLRTLVSSL RTLVSSLRTL VSSLRTLVSS LRTLVSSLRT LVSSLRKKKK 60
KKKC                                                             64

SEQ ID NO: 41           moltype = AA  length = 10
FEATURE                 Location/Qualifiers
source                  1..10
                        mol_type = protein
```

```
                    organism = synthetic construct
SITE                7..9
                    note = D-Arginine
SEQUENCE: 41
TLVSSLRRRG                                                              10

SEQ ID NO: 42       moltype = AA  length = 17
FEATURE             Location/Qualifiers
source              1..17
                    mol_type = protein
                    organism = synthetic construct
SITE                14..16
                    note = D-Arginine
SEQUENCE: 42
TLVSSLKTLV SSLRRRG                                                      17

SEQ ID NO: 43       moltype = AA  length = 16
FEATURE             Location/Qualifiers
source              1..16
                    mol_type = protein
                    organism = synthetic construct
SITE                1..3
                    note = D-Arginine
SITE                4
                    note = D- Glutamic acid
SITE                5
                    note = D-Leucine
SITE                9
                    note = D-Leucine
SITE                6..7
                    note = D-Serine
SITE                8
                    note = D- Valine
SITE                10
                    note = D-Threonine
SITE                11
                    note = D-Leucine
SITE                15
                    note = D-Leucine
SITE                12..13
                    note = D-Serine
SITE                14
                    note = D- Valine
SITE                16
                    note = D-Threonine
SEQUENCE: 43
RRRELSSVLT LSSVLT                                                       16
```

PHOSPHATIDYLSERINE-BINDING CONJUGATES

RELATED APPLICATION

This application claims priority to U.S. Provisional Application Ser. No. 63/295,462, filed Dec. 30, 2021, the disclosures of which are hereby incorporated by reference in their entirety.

REFERENCE TO AN ELECTRONIC SEQUENCE LISTING

The contents of the electronic sequence listing (087533-0572702.xml; Size: 113,552 bytes; and Date of Creation: Apr. 10, 2023) are herein incorporated by reference in its entirety.

FIELD OF THE INVENTION

Embodiments of the invention are related to phosphatidylserine-binding (PS-binding) conjugates capable of activating or stimulating Toll-like receptors (TLRs), and to methods of using these conjugates for treating cancer.

SUMMARY

One aspect of the present disclosure relates to a phosphatidylserine-binding (PS-binding) conjugate, wherein the conjugate comprises at least one PS-binding domain, and wherein the conjugate includes at least one Toll-like Receptor binding (TLR-binding) domain.

Another aspect of the present disclosures relates to a method of treating a subject with cancer comprising administering to the subject a conjugate as disclosed herein.

BRIEF DESCRIPTION OF THE DRAWINGS

FIG. 4A shows exemplary growth curves of the subcutaneously implanted CT-26 mouse colon cancer cell line in syngeneic BALB/c mice. This figure shows further tumor growth suppression to Cisplatin+CBP501+anti-CTLA4 treatment by the addition of TSA005 or TSA006. In this figure, "ip" stands for "intraperitoneal injection", and "iv" stands for "intravenous injection". FIGS. 4B-4D show individual tumor growth curves of the experiments shown in FIG. 4A (FIG. 4B: CDDP+501+aCTLA4+Saline treatment, FIG. 4C: CDDP+501+aCTLA4+TSA005 treatment, FIG. 4D: CDDP+501+aCTLA4+TSA006 treatment).

DETAILED DESCRIPTION

Figure 1:
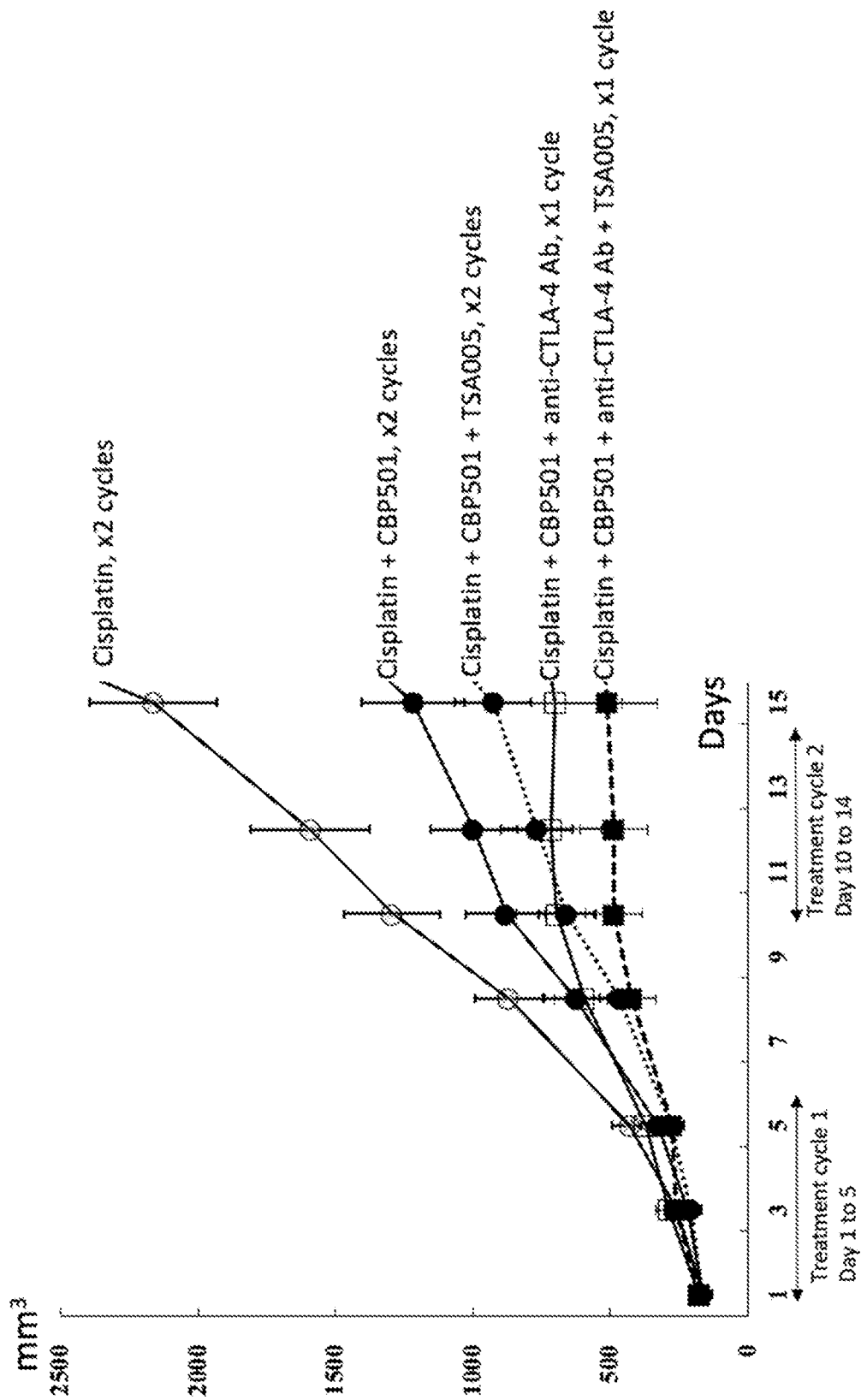
FIG. 1 is a graph showing exemplary growth curves of the syngeneic subcutaneous tumor, CT26 colon cancer cell line, of BALB/c mice treated with cisplatin, CBP501, anti-CTLA-4 antibody, TSA005 and/or vehicle, for one or more cycles.

Success of immune checkpoint inhibitors, namely anti-CTLA4, anti-PD1, and anti-PDL1 antibodies, have established immune therapy as a fifth pillar to fight against cancer in addition to surgery, radiotherapy, chemotherapy, and molecular targeted therapy (ref 1). Antibodies and genetically modified T-cells that leverage the function of T cells are under investigation. Some of these therapies have already been approved, or are soon to be approved by US FDA as anti-cancer medicines (ref 2).

The action of these immunologic agents that leverage T cells tends to be robust and has been shown to significantly ameliorate survival and patient prognosis. However, these treatments appear to only work in a minority of patients. Therefore, there are still large unmet medical needs (ref 1).

T cells belong to one of the two major immune systems in mammals and humans, namely, the adaptive immune system. The adaptive immune system, also referred as the acquired immune system, is a subsystem of the immune system that is composed of specialized, systemic cells and processes that eliminate pathogens or prevent their growth. The acquired immune system is one of the two main immunity strategies found in vertebrates (the other being the innate immune system). Like the innate system, the adaptive immune system includes both humoral immunity components and cell-mediated immunity components and destroys invading pathogens. Unlike the innate immune system, which is pre-programmed to react to common broad categories of pathogens, the adaptive immune system is highly specific to each particular pathogen the body has encountered.

The innate immune system is an older evolutionary defense strategy, relatively speaking. The major functions of the innate immune system are to recruit immune cells to infection sites by producing chemical factors, including chemical mediators such as cytokines, activate the complement cascade to identify bacteria, activate cells, and promote clearance of antibody complexes or dead cells, identify and remove foreign substances present in organs, tissues, blood and lymph, by specialized white blood cells, and activate the adaptive immune system through antigen presentation.

The innate immune system tends to be activated before the adaptive immune system, and to initiate and/or enhance its activity. Among the components of the innate immune system, Toll-like receptors (TLRs) have been considered to be interesting candidates for inducing the activation of the immune system against cancer. To date, many compounds have been investigated in the basic research field and many of them have been in human clinical trials (ref 3). Many TLR agonists have shown promising anti-cancer activities in animal models, however, many of them have yet to show efficacy in clinical studies. Some of the reasons for the failure of the TLR agonists in clinical studies are systemic toxicities and/or lack of activities at the tolerable doses (ref 4).

Methods of targeting tumors with antibodies have been successful in many cancer types. However, these methods have proven to be less effective when treating solid tumors, because it is believed that large molecules such as these tend not to penetrate dense interstitial tissues (ref 7).

To overcome this issue, the present invention provides compounds comprising phosphatidylserine (PS) binding peptides that target apoptotic cells to deliver TLR agonists to the tumor site. Once bound, such conjugates trigger phagocytosis of the apoptotic cell by antigen presenting cells (APCs). This allows the anti-cancer agent to work against a variety of tumors alone or in combination with other anti-tumor agents that are expected to induce apoptosis of tumor cells and/or work through the adoptive immune system.

Phosphatidylserine (PS) is predominantly confined to the inner leaflet of plasma membrane in cells, but it is externalized on the cell surface during apoptosis. Externalized PS is required for effective phagocytosis of apoptotic cells by macrophages. Such phagocytosis is believed to silence the immune system to the antigens contained in the cells undergoing phagocytosis. It is also believed that this is one of the mechanisms that cancer cells may use to evade immune surveillance. By being subject to phagocytosis by macrophages, large numbers of dying cancer cells would not trigger any antigen-specific response from the immune system (ref 8).

Here, to the present invention activates an immune reaction to the antigens present in apoptotic and/or dying cells, wherein the antigens presumably include neoantigens found in cancer cells, by conjugating TLR agonists to PS-binding peptides.

One aspect of the present disclosure relates to a phosphatidylserine-binding (PS-binding) conjugate, wherein the conjugate comprises at least one PS-binding domain, and wherein the conjugate includes at least one Toll-like Receptor binding (TLR-binding) domain.

As used herein, the term "conjugated" when referring to two moieties means the two moieties are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der waal's bond(s)/interactions, hydrogen bond(s), polar bond(s), or combinations or mixtures thereof).

In some embodiments, the PS-binding domain is a peptide sequence, non-limiting examples of which are LIKKPF (SEQ ID NO:1), PGDLSR (SEQ ID NO:2), CLIKKPF (SEQ ID NO:3), CPGDLSR (SEQ ID NO:4), FNFRLKAGA-KIRFG (SEQ ID NO:5), FXFXLKXXXKXR (SEQ ID NO:6), TLVSSL (SEQ ID NO:7), CLSYYPSYC (SEQ ID NO:8), GEGKGGr (SEQ ID NO:9), gegkggr (SEQ ID NO:10), GEGr (SEQ ID NO:11), gegr (SEQ ID NO:12), GE, ge, RGEGR (SEQ ID NO:13), rgegr (SEQ ID NO:14), and Cyclo(RKKWFGC) (SEQ ID NO:15); wherein a capital letter indicates a L-amino acid, and a non-capitalized letter indicates a D-amino acid, and wherein "X" represents any L-amino acid. In some embodiments, the PS-binding peptide sequence is GEGKGGr (SEQ ID NO:9).

In some embodiments, the structure of TSA006 is (GEGKGGr)4-K2-K-Cys(MI-CL264)-NH2. In some embodiments, the structure of TSA029 is (RGEGR)4-K2-K-Cys(MI-CL264)-NH2.

In some embodiments, the PS-binding peptide sequence is 50%, 55%, 60%, 65%, 70%, 75%, 80%, 85%, 90%, 95%, 96%, 97%, 98%, or 99% identical to TLVSSL (SEQ ID NO:7).

In some embodiments, the PS-binding peptide sequence is 50%, 55%, 60%, 65%, 70%, 75%, 80%, 85%, 90%, 95%, 96%, 97%, 98%, or 99% identical to GEGKGGr (SEQ ID NO:9), wherein a capital letter indicates a L-amino acid, and a non-capitalized letter indicates a D-amino acid.

As used herein, the terms "capable of binding" or "binding" as used herein refers to a moiety (e.g., a compound as described herein) that is able to measurably bind to a target (e.g., a phosphatidylserine, or a Toll-like receptor protein). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

In some embodiments, the TLR-binding domain is a TLR agonist, non-limiting examples of which are Pam3Cys, PAM3CSK4, PAM3CSK4, SMP-105, CBLB612, IPH 3102, ARNAX, MPLA, MALP-2, Zymosan, Poly (I:C), Poly-ICLC, Poly-IC12U, GLA-SE, BNT411, AS04, AS15, OK-432, CBLB502, M-VM3, Bistriazolyl, VTX1463, MGN1703, CpG-7909, IM02055, dSLIM, SD-101, KSK-CpG, ODN M362, CpG-1826, LPS, Flagellin, Imiquimod, Motolimod, Rintatolimod, CL264, Imidazoquinoline, Resiquimod, Tilsotolimod, UC-1Vi50, CADI-05, GNKG168, R07119929, SHR2150, TransCon, CMP-001, and CpG ODN.

As used herein, the terms "Toll-like receptors" and "TLRs" refer to a class of proteins that play a key role in the innate immune system. TLRs are single-pass membrane-spanning receptors usually expressed on sentinel cells such as macrophages and dendritic cells, that recognize structurally conserved molecules derived from microbes. Once these microbes have breached physical barriers such as the skin or intestinal tract mucosa, they are recognized by TLRs, which activate immune cell responses. The TLRs include TLR1, TLR2, TLR3, TLR4, TLR5, TLR6, TLR7, TLR8, TLR9, TLR10, TLR11, TLR12, and TLR13. Humans lack genes for TLR11, TLR12 and TLR13[1] and mice lack a functional gene for TLR10. TLR1, TLR2, TLR4, TLR5, TLR6, and TLR10 are located on the cell membrane, whereas TLR3, TLR7, TLR8, and TLR9 are located in intracellular vesicles, because they are sensors of nucleic acids The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

In some embodiments, the conjugate comprises more than one PS-binding peptide sequences. In some embodiments, the conjugate comprises more than two PS-binding peptide sequences. In some embodiments, the conjugate comprises a dimer of the same PS-binding sequence. In some embodiments, the conjugate comprises a trimer of the same PS-binding sequence. In some embodiments, the conjugate comprises a tetramer of the same PS-binding sequence. In some embodiments, the conjugate comprises a pentamer of the same PS-binding sequence. In some embodiments, the conjugate comprises an hexamer of the same PS-binding sequence. In some embodiments, the conjugate comprises a heptamer of the same PS-binding sequence. In some embodiments, the conjugate comprises a octamer of the same PS-binding sequence. In some embodiments, the conjugate comprises a nonamer of the same PS-binding sequence. In some embodiments, the conjugate comprises a decamer of the same PS-binding sequence. In some embodiments, the conjugate comprises an undecamer of the same PS-binding sequence. In some embodiments, the conjugate comprises a dodecamer of the same PS-binding sequence. In some embodiments, the conjugate comprises a tetramer of TLVSSL (SEQ ID NO:7), wherein a capital letter indicates a L-amino acid, and a non-capitalized letter indicates a D-amino acid. In some embodiments, the conjugate comprises a tetramer of GEGKGGr (SEQ ID NO:9), wherein a capital letter indicates a L-amino acid, and a non-capitalized letter indicates a D-amino acid.

In some embodiment, the conjugate comprises one or more retro-inverso of any of the PS-binding peptide disclosed herein.

The term "retro-inverso" refers to linear peptides whose amino acid sequence is reversed and the α-center chirality of the amino acid subunits is inverted as well. Usually, these types of peptides are designed by including D-amino acids in the reverse sequence to help maintain side chain topology similar to that of the original L-amino acid peptide and make them more resistant to proteolytic degradation. Other reported synonyms for these peptides in the scientific literature are: Retro-Inverso Peptides, All-D-Retro Peptides, Retro-Enantio Peptides, Retro-Inverso Analogs, Retro-Inverso Analogues, Retro-Inverso Derivatives, and Retro-Inverso Isomers. D-amino acids represent conformational mirror images of natural L-amino acids occurring in natural proteins present in biological systems. Peptides that contain D-amino acids have advantages over peptides that just contain L-amino acids. In general, these types of peptides are less susceptible to proteolytic degradation and have a longer effective time when used as pharmaceuticals. Furthermore, the insertion of D-amino acids in selected sequence regions as sequence blocks containing only D-amino acids or in-between L-amino acids allows the design of peptide-based drugs that are bioactive and possess increased bioavailability in addition to being resistant to proteolysis. Furthermore, if properly designed, retro-inverso peptides can have binding characteristics similar to L-peptides. Retro-inverso peptides are useful candidates for the study of protein-protein interactions by designing peptidomimetics that mimic the shape of peptide epitopes, protein-protein, or protein-peptide interfaces. Retro-inverso-peptides are attractive alternatives to L-peptides used as pharmaceuticals. These of peptide have been reported to elicit lower immunogenic responses compared to L-peptides. In the present disclosure, L-amino acids are represented by capital letters, and D-amino acid are represented by non-capitalized letters.

In some embodiments, the TLR agonist is selected from the group consisting of: In some embodiments, the TLR agonist is CL264. In some embodiments, the TLR-binding domain is the TLR agonist CL264.

In some embodiments, the conjugate comprises a linker moiety linking the PS-binding domain to the TLR-binding domain. In some embodiments, the linker moiety is a short amino acid sequence (or "amino acid linker") created in nature to separate multiple domains in a single protein. Most of amino acid linkers are rigid and function to prohibit unwanted interactions between the discrete domains, but other linkers, such as "Gly-rich" linkers, are flexible, connecting various domains in a single protein without interfering with the function of each domain. Numerous amino acid linkers are known in the art, for instance in the publication by Reddy Chichili V P et al. ("Linkers in the structural biology of protein-protein interactions." Protein Sci. 2013; 22(2):153-167. doi:10.1002/pro.2206). Modifications to known amino acid linkers are possible, such as the use of non-natural amino acids or non-proteinogenic amino acids. For instance, a linker moiety can comprise ornithine, 2,4-diaminobutyric acid and/or 2,3-diaminopropanoic acid. In some embodiments, the linker moiety does not comprise any amino acid.

Another aspect of the present disclosures relates to a method of treating a subject with cancer comprising administering to the subject a conjugate as disclosed herein.

In some embodiments, the cancer is a solid tumor. Non-limiting examples of solid tumors include sarcomas, carcinomas, and lymphomas. Solid tumor can also be identified based on the organ from which they originate, such as the brain, lung, esophagus, stomach, pancreas, or liver of a subject. In some embodiments, a solid tumor is a mesothelioma. In some embodiments, the cancer is a blood-based cancer. In some embodiments, cancer is multiple myeloma. In some embodiments, the cancer is colon cancer. In some embodiments, the cancer is leukemia.

As used herein, the term "cancer" refers to all types of cancer, neoplasm or malignant tumors found in mammals (e.g., humans), including leukemias, lymphomas, carcinomas and sarcomas. Exemplary cancers that may be treated with a compound or method provided herein include brain cancer, glioma, glioblastoma, neuroblastoma, prostate cancer, bladder cancer, urothelial cancer, gallbladder cancer, colorectal cancer, pancreatic cancer, medulloblastoma, skin cancer, melanoma, cervical cancer, gastric cancer, esophageal cancer, liver cancer, endometrial cancer, ovarian cancer, lung cancer, cancer of the head and neck, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, esophagus, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, soft tissue sarcoma, osteo-sarcoma, primary thrombocytosis, primary macroglobulinemia, primary brain tumors, malignant pancreatic insulinoma, neuroendocrine tumor, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

Invention methods and uses include administering an amount of a conjugate disclosed herein effective to treat the tumor or cancer. In particular aspects, a method or use inhibits or reduces relapse, growth, progression, worsening or metastasis of the tumor or cancer; results in partial or complete destruction of the neoplastic, tumor, cancer or malignant cell mass, volume, size or numbers of cells, stimulating, inducing or increasing neoplastic, tumor, cancer or malignant cell necrosis, lysis or apoptosis, reducing neoplasia, tumor, cancer or malignancy volume size, cell mass, inhibiting or preventing progression or an increase in neoplasia, tumor, cancer or malignancy volume, mass, size or cell numbers, or prolonging lifespan; results in reducing or decreasing severity, duration or frequency of an adverse symptom or complication associated with or caused by the neoplasia, tumor, cancer or malignancy; or method results in reducing or decreasing pain, discomfort, nausea, weakness or lethargy, or results in increased energy, appetite, improved mobility or psychological well-being.

As used herein, the term "apoptosis" refers to programmed cell death, and associated changes in cell physiology, e.g., nucleic acid fragmentation, caspase activation, etc., as is understood in the art. The term "catastrophe" means cell death resulting from an error in the mitotic process. In catastrophe, there are fewer features present that are characteristic of apoptosis e.g., caspase activation, chromosome condensation, etc.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

In some embodiments, the subject is a mammal. In some embodiments, the subject is human.

As used herein, the terms "patient", "subject" or "subject in need thereof" refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, cats and other non-mammalian animals. In some embodiments, a subject is human.

In some embodiments, the method further comprises administering to the subject an anti-cancer agent, and/or an immunologic agent. In some embodiments, the method further comprises administering to the subject an anti-cancer agent, and an immunologic agent. In some embodiments, the method further comprises administering to the subject an anti-cancer agent, or an immunologic agent.

As used herein, the term "immunologic agent" refers to drugs or compounds that can modify the immune response, either by enhancing or suppressing the immune system.

They are used to fight infections, prevent and treat certain diseases. Immunologic agents include drugs used for immunosuppression to prevent graft rejection. They can be used as cancer chemotherapy agents.

An "anti-cancer agent" or "anticancer agent" as used herein refers to a molecule (e.g., compound, peptide, protein, or nucleic acid) used to treat cancer through destruction or inhibition of cancer cells or tissues. Anticancer agents may be selective for certain cancers or certain tissues. In embodiments, anticancer agents herein may include epigenetic inhibitors and multi-kinase inhibitors. In some embodiments, the anti-cancer agent is a serine threonine kinase inhibitor.

"Anti-cancer agent" and "anticancer agent" are used in accordance with their plain ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g., U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec.RTM.), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g., Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g., Altorhyrtin A and Altorhyrtin C), Spongistatins (e.g., Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g., Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e.

T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Carib-aeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Gudrin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), immunotherapy (e.g., cellular immunotherapy, antibody therapy, cytokine therapy, combination immunotherapy, etc.), radioimmunotherapy (e.g., anti-CD20 monoclonal antibody conjugated to 111In, 90Y, or 131I, etc.), immune checkpoint inhibitors (e.g., CTLA4 blockade, PD-1 inhibitors, PD-L1 inhibitors, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™), erlotinib (Tarceva™), cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

In some embodiments, the anti-cancer agent is a serine/threonine kinase inhibitor, non-limiting examples of which are (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) (SEQ ID NO:16), (d-Arg)(d-Arg)(d-Arg)(d-Gln)(d-Arg)(d-Arg)(d-Bpa)(d-Ser)(d-Trp)(d-Ser)(d-Phe-2,3,4,5,6-F)(d-Cha) (SEQ ID NO:17), (d-Bpa)(d-Ser)(d-Trp)(d-Ser)(d-Phe-2,3,4,5,6-F)(d-Cha)(d-Arg)(d-Arg)(d-Gln)(d-Arg)(d-Arg)(d-Arg) (SEQ ID NO:18), (d-Arg)(d-Arg)(d-Gln)(d-Arg)(d-Arg)(d-Arg)(d-Bpa)(d-Ser)(d-Trp)(d-Ser)(d-Phe-2,3,4,5,6-F)(d-Cha) (SEQ ID NO:19), (d-Cha)(d-Phe-2,3,4,5,6-F)(d-Ser)(d-Trp)(d-Ser)(d-Bpa)(d-Arg)(d-Arg)(d-Arg)(d-Gln)(d-Arg)(d-Arg) (SEQ ID NO:20), (d-Arg)(d-Arg)(d-Arg)(d-Gln)(d-Arg)(d-Arg)(d-Cha)(d-Phe-2,3,4,5,6-F)(d-Ser)(d-Trp)(d-Ser)(d-Bpa) (SEQ ID NO:21), (d-Cha)(d-Phe-2,3,4,5,6-F)(d-Ser)(d-Trp)(d-Ser)(d-Bpa)(d-Arg)(d-Arg) (d-Gln) (d-Arg) (d-Arg) (d-Arg) (SEQ ID NO:22), (d-Arg) (d-Arg) (d-Gln) (d-Arg) (d-Arg) (d-Arg) (d-Cha) (d-Phe-2,3,4,5,6-F) (d-Ser)(d-Trp)(d-Ser) (d-Bpa) (SEQ ID NO:23), (d-Arg) (d-Arg) (d-Arg) (d-Arg) (d-Arg) (d-Arg) (d-Cha) (d-Phe-2,3,4,5,6-F) (d-Ser) (d-Trp)(d-Ser)(d-Bpa) (SEQ ID NO:24), (d-Cha)(d-Phe-2,3,4,5,6-F) (d-Ser) (d-Trp)(d-Ser)(d-Bpa)(d-Arg)(d-Arg) (d-Arg) (d-Arg) (d-Arg) (d-Arg) (SEQ ID NO:25), (d-Arg) (d-Arg) (d-Arg) (d-Arg) (d-Arg) (d-Arg) (d-Bpa) (d-Ser)(d-Trp)(d-Ser) (d-Phe-2,3,4,5,6-F)(d-Cha) (SEQ ID NO:26), (d-Bpa) (d-Ser) (d-Trp)(d-Ser) (d-Phe-2,3,4,5,6-F)(d-Cha) (d-Arg) (d-Arg) (d-Arg) (d-Arg) (d-Arg) (d-Arg) (SEQ ID NO:27), (d-Arg)(d-Arg)(d-Bpa) (d-Arg) (d-Arg) (d-Arg) (d-Phe-2,3,4,5,6-F)(d-Cha) (SEQ ID NO:28) (d-Cha) (d-Phe-2,3,4,5,6-F) (d-Arg) (d-Arg) (d-Arg) (d-Bpa) (d-Arg)(d-Arg) (SEQ ID NO:29) (d-Arg) (d-Arg) (d-Arg) (d-Bpa) (d-Arg)(d-Trp) (d-Arg) (d-Phe-2,3,4,5,6-F) (d-Cha) (SEQ ID NO:30), (d-Cha) (d-Phe-2,3,4,5,6-F) (d-Arg)(d-Trp) (d-Arg) (d-Bpa) (d-Arg) (d-Arg) (d-Arg) (SEQ ID NO:31), (d-Arg)(d-Arg)(d-Arg)(d-Arg)(d-Bpa) (d-Arg)(d-Trp)(d-Arg) (d-Phe-2,3,4,5,6-F) (d-Cha) (SEQ ID NO:32), (d-Cha) (d-Phe-2,3,4,5,6-F) (d-Arg) (d-Trp)(d-Arg) (d-Bpa) (d-Arg) (d-Arg) (d-Arg) (d-Arg) (SEQ ID NO:33), (d-Arg) (d-Arg)(d-Arg)(d-Bpa)(d-Arg)(d-Arg) (d-Arg) (d-Phe-2,3,4,5,6-F)(d-Cha) (SEQ ID NO:34), and (d-Cha) (d-Phe-2,3,4,5,6-F) (d-Arg) (d-Arg) (d-Arg) (d-Bpa) (d-Arg) (d-Arg) (d-Arg) (SEQ ID NO:35).

In some embodiments, the serine/threonine kinase inhibitor is "CBP501", a peptide compound comprising (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) (SEQ ID NO:16). In some embodiments, CBP501 is a pharmaceutically salt. In some embodiments, CBP501 is a H-(D)p-benzoylphenylalanyl-(D)seryl-(D)tryptophanyl-(D)seryl-(D)pentafluorophenylalanyl-(D)cyclohexylalanyl-(D)arginyl-(D)arginyl-(D)arginyl-(D)glutaminyl-(D)arginyl-(D)arginine acetate salt.

In some embodiments, a method or use employs a T cell activating agent. Non-limiting examples of T cell activating agents include agents that target CD28 (cell differentiation antigen 28, also known as Tp44, T-cell-specific surface glycoprotein, CD28 antigen CD28 molecule), OX40 (Tumor Necrosis Factor Receptor Superfamily, Member 4, TNFRSF4, also known as OX40L Receptor, OX40 Antigen, TXGP1L), GITR (glucocorticoid-induced tumor necrosis factor receptor), CD137 (also known as 4-1BB), CD27 (also known as TNFRSF7, Tp55), and HVEM (Herpesvirus entry mediator, also known as CD270, TNFRSF14).

Representative T cell activating agents include ligands that bind to such targets, for example, CD28, OX40, GITR, CD137, CD27 and HVEM ligands. Representative T cell activating agents also include antibodies that bind to such targets, for example, anti-CD28, anti-OX40, anti-GITR, anti-CD137, anti-CD27 and anti-HVEM antibodies.

In some embodiments, a method or use employs an immune checkpoint inhibitor. Non-limiting examples of immune checkpoint inhibitors include agents that target CTLA-4 (cytotoxic T-lymphocyte-associated protein 4, also known as CD152), PD1 (Programmed Cell Death 1, also known as CD279, SLEB2, HPD-1, HSLE1), PDL1 (Programmed death-ligand 1, also known as CD274, B7-H1 (B7 homolog 1), Programmed Cell Death 1 Ligand 1, PDCD1 Ligand 1), PDL2 (programmed cell death 1 ligand 2), VISTA (V-domain Ig suppressor of T cell activation, also known as, B7-H5, Gi24, Diesl and SISP1), TIM3 (T cell immunoglobulin and mucin domain 3), LAG-3 (Lymphocyte-activation gene 3, also known as CD223) or BTLA (B- and T-lymphocyte attenuator, also known as CD272).

Representative immune checkpoint inhibitors include ligands that bind to such targets, for example, CTLA-4, PD1, PDL1, PDL2, VISTA, TIM3, LAG-3 and BTLA ligands. Representative immune checkpoint inhibitors, or immunologic agents, also include antibodies that bind to such targets, for example, anti-CTLA-4, anti-PD1, anti-PDL1, anti-PDL2, anti-VISTA, anti-TIM3, anti-LAG-3 and anti-BTLA antibodies.

In some embodiments, the immunologic agent is an antibody. In some embodiments, the immunologic agent is antibody that bind to an immune checkpoint inhibitor, non-limiting examples which include an anti-CTLA-4, anti-PD1, anti-PD-L1, anti-PDL2, anti-VISTA, anti-TIM3, anti-LAG-3 or anti-BTLA antibody. In some embodiments, the antibody is an anti-CTLA-4 antibody.

In some embodiments, the method further comprises administering a nucleic acid damaging agent or anti-proliferative agent, non-limiting examples of which include a platinum-containing drug, such as cis-platin, carboplatin, nedaplatin, mitaplatin, satraplatin, picoplatin, triplatin, miriplatin, or oxaliplatin. In some embodiments, the platinum-containing drug is cisplatin.

In some embodiments, methods and uses include or consist of administering a platinum-containing drug, cisplatin (cisplatin), carboplatin, oxaliplatin, pemetrexed, gemcitabine, 5-fiuorouracil (5-FU), rebeccamycin, adriamycin (ADR), bleomycin (Bleo), pepleomycin, cisplatin, cis-platinum, or cis-diamminedichloroplatinum(II) (CDDP), oxaliplatin, or camptotecin (CPT), cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) or a 5-azacytidine related compound, actinomycin D, mithramycin, mitomycin C, carmustine, lomustine, semustine, streptozotocin, hydroxyurea, cisplatin, mitotane, procarbazine, dacarbazine, a taxane, vinblastine, vincristine, doxorubicin, dibromomannitol, radiation or a radioisotope. Particular non-limiting examples of radiation include UVradiation, IR radiation, Xray, or alpha-, beta- or gamma-radiation. Particular non-limiting examples of radioisotopes include I131, I125, Sr89, Sm153, Y90, or Lu177.

Invention methods and uses are applicable to a cell proliferative or hyperproliferative disorder or undesirable cell proliferation. In particular embodiments, a cell proliferative disorder comprises a tumor or cancer. In more particular embodiments, a cell proliferative disorder comprises a metastatic tumor or cancer.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

In some embodiments, the dose administered to the subject is about 2 mg/kg or less every three weeks. In some embodiments, the dose administered to the subject is 2 mg/kg or less every three weeks. In some embodiments, the dose administered to the subject is at least 2 mg/kg every three weeks. In some embodiments, the dose administered to the subject is 2 mg/kg every three weeks. In some embodiments, the dose administered to the subject is from about 0.1 to about 10 mg/kg every three weeks. In some embodiments, the dose administered to the subject is about 1 mg/kg or less every two weeks. In some embodiments, the dose administered to the subject is 1 mg/kg or less every two weeks. In some embodiments, the dose administered to the subject is at least 1 mg/kg every two weeks. In some embodiments, the dose administered to the subject is 1 mg/kg every two weeks. In some embodiments, the dose administered to the subject is from about 0.1 to about 10 mg/kg every two weeks. In some embodiments, the dose administered to the subject is 1 mg/kg or less every week. In some embodiments, the dose administered to the subject is at least 1 mg/kg every week. In some embodiments, the dose administered to the subject is 1 mg/kg every week. In some embodiments, the dose administered to the subject is from about 0.1 to about 10 mg/kg every week.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the conjugate. In some embodiments, the administering includes the conjugate and an immunologic agent. In some embodiments, the administering includes the conjugate and an anti-cancer agent. In some embodiments, the administering includes the conjugate, an immunologic agent, and an anti-cancer agent. In some embodiments, the administering includes the conjugate, an immunologic agent, an anti-cancer agent, and a platinum-containing drug.

In some embodiments, the conjugate is administered intravenously. In some embodiments, the conjugate is administered intraperitoneally.

In some embodiments, the conjugate is administered to the subject every day. In some embodiments, the conjugate is administered to the subject every other day. In some embodiments, the conjugate is administered to the subject every three days. In some embodiments, the conjugate is administered to the subject every four days. In some embodiments, the conjugate is administered to the subject every five days. In some embodiments, the conjugate is administered to the subject every six days. In some embodiments, the conjugate is administered to the subject every seven days. In some embodiments, the conjugate is administered to the subject every eight days. In some embodiments, the conjugate is administered to the subject every nine days. In some embodiments, the conjugate is administered to the subject every ten days. In some embodiments, the conjugate is administered to the subject every eleven days. In some embodiments, the conjugate is administered to the subject every twelve days. In some embodiments, the conjugate is administered to the subject every thirteen days. In some embodiments, the conjugate is administered to the subject every fourteen days. In some embodiments, the conjugate is administered to the subject at least every fourteen days. In some embodiments, the conjugate is administered to the subject every month. In some embodiments, the conjugate is administered to the subject at least every month. In some embodiments, the conjugate is administered to the subject every two months. In some embodiments, the conjugate is administered to the subject at least every two months. [

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g., to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

In some embodiments, cytotoxic drugs are administered before the PS-binding conjugate. In some embodiments, cytotoxic drugs are administered at least one day before the PS-binding conjugate. In some embodiments, cytotoxic drugs are administered at least two days before the PS-binding conjugate. In some embodiments, cytotoxic drugs are administered at least three days before the PS-binding conjugate. In some embodiments, cytotoxic drugs are administered at least four day before the PS-binding conjugate. In some embodiments, cytotoxic drugs are administered at least five days before the PS-binding conjugate. In some embodiments, cytotoxic drugs are administered at least six days before the PS-binding conjugate. In some embodiments, cytotoxic drugs are administered at least one week before the PS-binding conjugate.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

Cancer model organism, as used herein, is an organism exhibiting a phenotype indicative of cancer, or the activity of cancer-causing elements, within the organism. The term cancer is defined above. A wide variety of organisms may serve as cancer model organisms, and include for example, cancer cells and mammalian organisms such as rodents (e.g., mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g., mice) and from humans.

The terms "immune response" and the like refer, in the usual and customary sense, to a response by an organism that protects against disease. The response can be mounted by the innate immune system or by the adaptive immune system, as well known in the art.

The terms "modulating immune response" and the like refer to a change in the immune response of a subject as a consequence of administration of an agent, e.g., a compound as disclosed herein, including embodiments thereof. Accordingly, an immune response can be activated or deactivated as a consequence of administration of an agent, e.g., a compound as disclosed herein, including embodiments thereof.

"B cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pre B cells, and further undergo immunoglobulin light chain rearrangement to become an immature B cells. Immature B cells include T1 and T2 B cells.

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

A "memory T cell" is a T cell that has previously encountered and responded to its cognate antigen during prior infection, encounter with cancer or previous vaccination. At a second encounter with its cognate antigen memory T cells can reproduce (divide) to mount a faster and stronger immune response than the first time the immune system responded to the pathogen.

A "regulatory T cell" or "suppressor T cell" is a lymphocyte which modulates the immune system, maintains tolerance to self-antigens, and prevents autoimmune disease.

An amino acid residue in a protein "corresponds" to a given residue when it occupies the same essential structural position within the protein as the given residue.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "fusion" or "chimera" and grammatical variations thereof, when used in reference to a sequence, means that the sequence contains one or more portions that are based upon, derived from, or obtained or isolated from, two or more different proteins. That is, for example, a portion of the sequence may be based upon or from one particular protein, and another portion of the sequence may be based upon or from a different particular protein. Thus, a fusion or chimeric polypeptide is a molecule in which different portions of the polypeptide are of different protein origins.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, in the form of either the neat base compound, or the base compound dissolved in a suitable inert solvent, or by treatment with an ion exchange resin. Non-limiting examples of pharmaceutically acceptable base addition salts include sodium, potassium, calcium, ammonium, organic amino, or magnesium salt, or a similar salt. In some embodiments, a pharmaceutically acceptable base addition salt is a compound comprising counterions to the conjugate. In some embodiments, a counterion to the conjugate is a cation, such as $Na^+$, $K^+$, $Ca^+$, $Mg^{2+}$, or $NH_4^+$. When compounds of the present disclosure contain relatively basic functionalities, acid addition salts can be obtained by contacting the neutral form of such compounds with a sufficient amount of the desired acid, in the form of either the neat acid compound or the acid compound dissolved in a suitable inert solvent, or by treatment with an ion exchange resin. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present disclosure contain both basic and acidic functionalities that allow the compounds to be converted into either base or acid addition salts. In some embodiments, the pharmaceutically acceptable salt is the trifluoroacetate salt derived by contacting trifluoroacetic acid, an acid with a relatively low boiling point (72.4° C.), with the neutral base form of the pharmaceutically active compound.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "synergistic amount" as used herein refers to the sum of a first amount (e.g., an amount of a compound provided herein) and a second amount (e.g., a therapeutic agent) that results in a synergistic effect (i.e. an effect greater than an additive effect).

Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the compound provided herein when used separately from the therapeutic agent. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the therapeutic agent when used separately from the compound provided herein.

In this disclosure, "comprises," "comprising," "containing" and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Example 1

Introduction

There are multiple peptides known to bind cell surface PS such as LIKKPF (SEQ ID NO:1), PGDLSR (SEQ ID NO:2) (ref 9), CLIKKPF (SEQ ID NO:3), CPGDLSR (SEQ ID NO:4) (ref 10), FNFRLKAGAKIRFG (SEQ ID NO:5) (ref 11), FXFXLKXXXKXR (SEQ ID NO:6) (ref 12), TLVSSL (SEQ ID NO:7) (ref 13), CLSYYPSYC (SEQ ID NO:8) (ref 14), and Cyclo(RKKWFGC) (SEQ ID NO:15) (ref 19). However, the affinity of these peptides to PS are not high enough to make them ideal target delivery tools by themselves.

We thought that making multivalent versions of these could overcome issue of low affinity and they still should be small enough to penetrate to solid tumors.

Our prediction was right in that monomer or dimer of the phosphoserine binding peptides conjugated to a TLR agonist did not show any anti-tumor activities, whereas a tetramer of TLVSSL (SEQ ID NO:7) has shown strong anti-tumor activities in mice while lacking any obvious systemic adverse activities.

Materials and Methods

Syngeneic Mice Model, TSA005 (FIG. 1)

All animal studies were conducted according to protocols approved by institutional animal care committee of CanBas Co., Ltd. Six-week-old female BALB/c mice (The Jackson Laboratories Japan, Inc., Kanagawa, Japan) were inoculated subcutaneously in a flank with a suspension of CT26WT cells ($5 \times 10^5$ cells). Ten days later mice were apportioned into 5 groups (6-8 mice/group) and treatments were initiated on day1.

The first cycle of the treatments was on day 1 to 5 and the second cycle was on day 10 to 14 as follows.

Cisplatin: Intravenous injection (i.v.) of Cisplatin 4 mg/kg and 5% Glucose on Day 1 and 10. Saline i.v. on Days 2, 3, 11 and 12.

Cisplatin+CBP501: Cisplatin 4 mg/kg and CBP501 6 mg/kg i.v. on Day 1 and 10. Saline i.v. on Days 2, 3, 11 and 12.

Cisplatin+CBP501+TSA005: Cisplatin 4 mg/kg and CBP501 6 mg/kg i.v. on Day 1 and 10. TSA005 100 µg i.v. on Days 2, 3, 11 and 12.

Cisplatin+CBP501+anti-CTLA-4 antibody: anti-CTLA4 antibody 200 µg intraperitoneal injection (i.p.) on Days 1 and 5. Cisplatin 4 mg/kg and CBP501 6 mg/kg i.v. on Day 2.

Cisplatin+CBP501+anti-CTLA-4 antibody+TSA005: anti-CTLA4 antibody 200 µg i.p. on Days 1 and 5. Cisplatin 4 mg/kg and CBP501 6 mg/kg i.v. on Day 2. TSA005 100 µg i.v. twice on Day 3 and once on Day 4.

Diphenhydramine 10 mg/kg was given i.p. 15 min before CBP501 or 5% Glucose treatment. The size of tumor was measured thrice weekly with a pair of calipers to calculate tumor volume by using the following formula: volume $(mm^3) = [(width)^2 \, (mm) \times length \, (mm)]/2$.

FIG. 1 shows growth curves of the syngeneic subcutaneous tumor, CT26 colon cancer cell line, of BALB/c mice treated with cisplatin, CBP501, anti-CTLA-4 antibody, TSA005 and/or vehicle.

Colon cancer cells from the CT26 cell line were subcutaneously inoculated in BALB/c mice $5 \times 10^5$ cells/mouse. The treatment was initiated on day 1, when the tumor sizes of 6-8 mice per test group attained an average size of about 200 mm³. A cycle of the treatment schedule, dose and the route of treatment are detailed below.

Treatment groups and schedule
  Group 1: Dya1 & 10: Cisplatin 4 mg/kg and 5% Glucose, intravenous (i.v.)
    Day 2, 3, 11 & 12: Saline, i.v.
  Group 2: Day 1 & 10: Cisplatin 4 mg/kg and CBP501 6 mg/kg, i.v.
    Day 2, 3, 11 & 12: Saline, i.v.
  Group 3: Day 1 & 10: Cisplatin 4 mg/kg and CBP501 6 mg/kg, i.v.
    Day 2, 3, 11, & 12: TSA005 100 µg, i.v.
  Group 4: Day 1: anti-CTLA-4, intraperitoneal injection (i.p.)
    Day 2: Cisplatin 4 mg/kg and CBP501 6 mg/kg, i.v.
    Day 5: anti-CTLA-4, i.p.
  Group 5: Day 1: anti-CTLA-4, i.p.
    Day 2: Cisplatin 4 mg/kg and CBP501 6 mg/kg, i.v.
    Day 3: TSA005 100 µg, twice, i.v.
    Day 4: TSA005 100 µg, once, i.v.
    Day 5: anti-CTLA-4, i.p.

Peptides

Table 1 below shows structure of PS-binding or non-sense control peptides conjugated with TLR-agonist or immuno-fluorescent molecule. In this table, a capital letter indicates a L-amino acid, and a non-capitalized letter indicates a D-amino acid.

TABLE 1

| Code name: Structure | Feature |
|---|---|
| TSA001:<br>CL264-rrrlssvlt | mono-retroinverso<br>of TLVSSL<br>(SEQ ID NO: 7) |
| TSA002:<br>TLVSSLrrrG-EDA-CL264 | mono-TLVSSL<br>(SEQ ID NO: 7) |
| TSA003:<br>CL264-rrre(lssvlt-NH2)lssvlt-NH2 | di-retroinverso<br>of TLVSSL<br>(SEQ ID NO: 7) |
| TSA004:<br>TLVSSLK(TLVSSL)rrrG-EDA-CL264 | di-TLVSSL<br>(SEQ ID NO: 7) |
| TSA005:<br>(TLVSSLr)4-K2-K-Cys(MI-CL264)-NH2 | tetra-TLVSSL<br>(SEQ ID NO: 7) |
| TSA006:<br>(GEGKGGr)4-K2-K-Cys(MI-CL264)-NH2 | tetra-GEGKGGr<br>(SEQ ID NO: 9) |
| TSA007:<br>CL264-CLSYYPSYC | mono-CLSYYPSYC<br>(SEQ ID NO: 8) |
| TSA008:<br>FITC replaces CL264 in tetra-TLVSSL | FITC replaces CL264 in tetra-TLVSSL<br>(SEQ ID NO: 7) |
| TSA009:<br>(TLVSSLr)8-K4-K2-K-Cys(MI-CL264)-NH2 | octa-TLVSSL<br>(SEQ ID NO: 7) |

Figure 2:
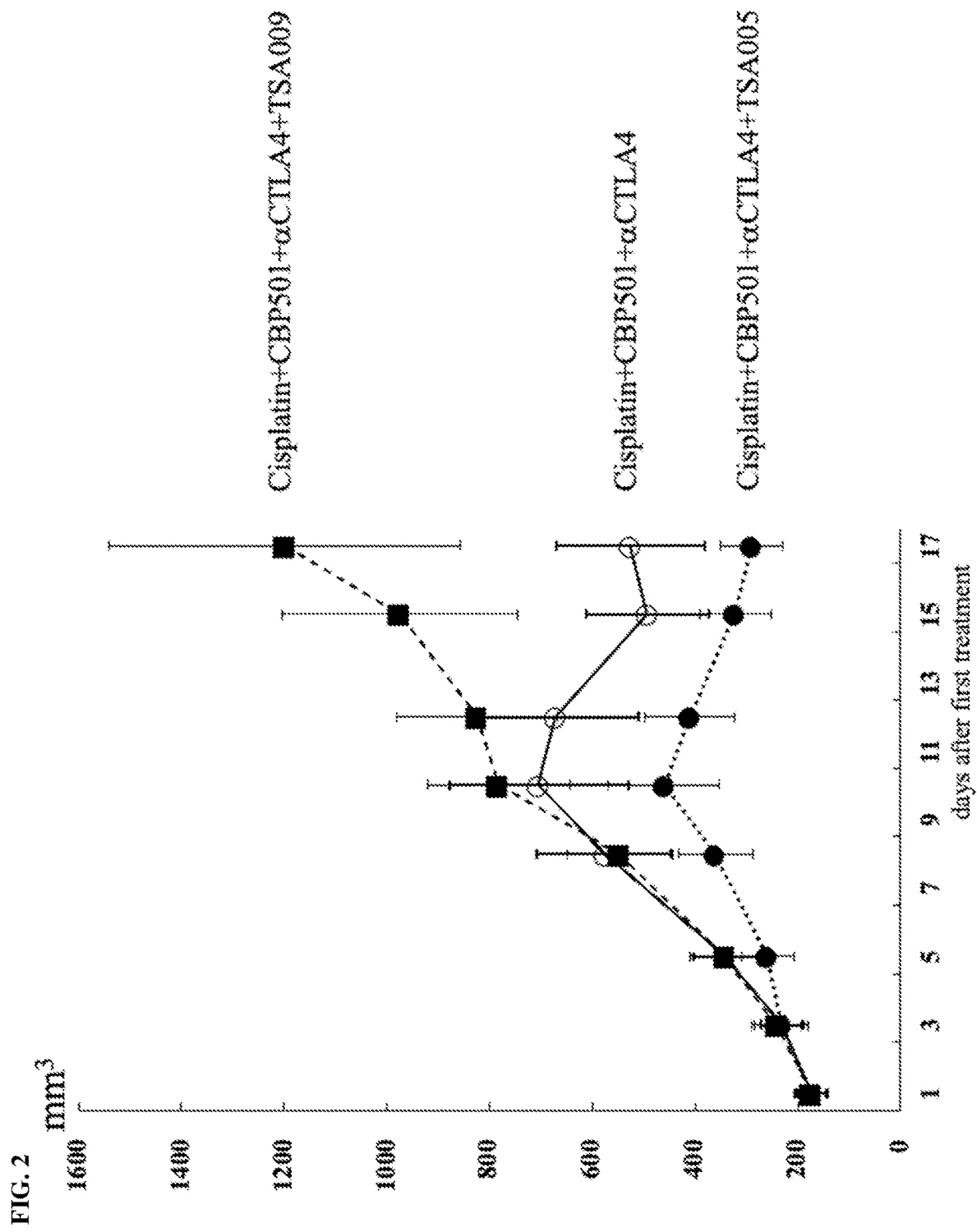
FIG. 2 is a graph showing exemplary growth curves of the syngeneic subcutaneous tumor, CT26 colon cancer cell line, of BALB/c mice treated with cisplatin, CBP501, anti-CTLA-4 antibody, with TSA005, TSA009 or vehicle, for one cycle.

Syngeneic Mice Model—TSA005 Compared to TSA009 (FIG. 2)

All animal studies were conducted according to protocols approved by institutional animal care committee of CanBas Co., Ltd. Six-week-old female BALB/c mice (The Jackson Laboratories Japan, Inc., Kanagawa, Japan) were inoculated subcutaneously in a flank with a suspension of CT26WT cells (5×10⁵ cells). Ten days later, the mice were apportioned into 3 groups (6 mice/group) and treatments were initiated on Day 1.

Cisplatin+CBP501+anti-CTLA-4 antibody: anti-CTLA4 antibody 200 µg intraperitoneal injection (i.p.) on Days 3 and 5. Cisplatin 4 mg/kg and CBP501 6 mg/kg i.v. on Day 2. Saline i.v. twice on Day 3 and once on Day 4.

Cisplatin+CBP501+anti-CTLA-4 antibody+TSA005: anti-CTLA4 antibody 200 µg i.p. on Days 3 and 5. Cisplatin 4 mg/kg and CBP501 6 mg/kg i.v. on Day 2. TSA005 100 µg i.v. twice on Day 3 and once on Day 4.

Cisplatin+CBP501+anti-CTLA-4 antibody+TSA009: anti-CTLA4 antibody 200 µg i.p. on Days 3 and 5. Cisplatin 4 mg/kg and CBP501 6 mg/kg i.v. on Day 2. TSA005 100 µg i.v. twice on Day 3 and once on Day 4.

Diphenhydramine 10 mg/kg was given i.p. 15 min before CBP501 or 5% Glucose treatment. The size of tumor was measured thrice weekly with a pair of calipers to calculate tumor volume by using the following formula: volume (mm³)=[(width)2 (mm)×length (mm)]/2.

Figure 3:
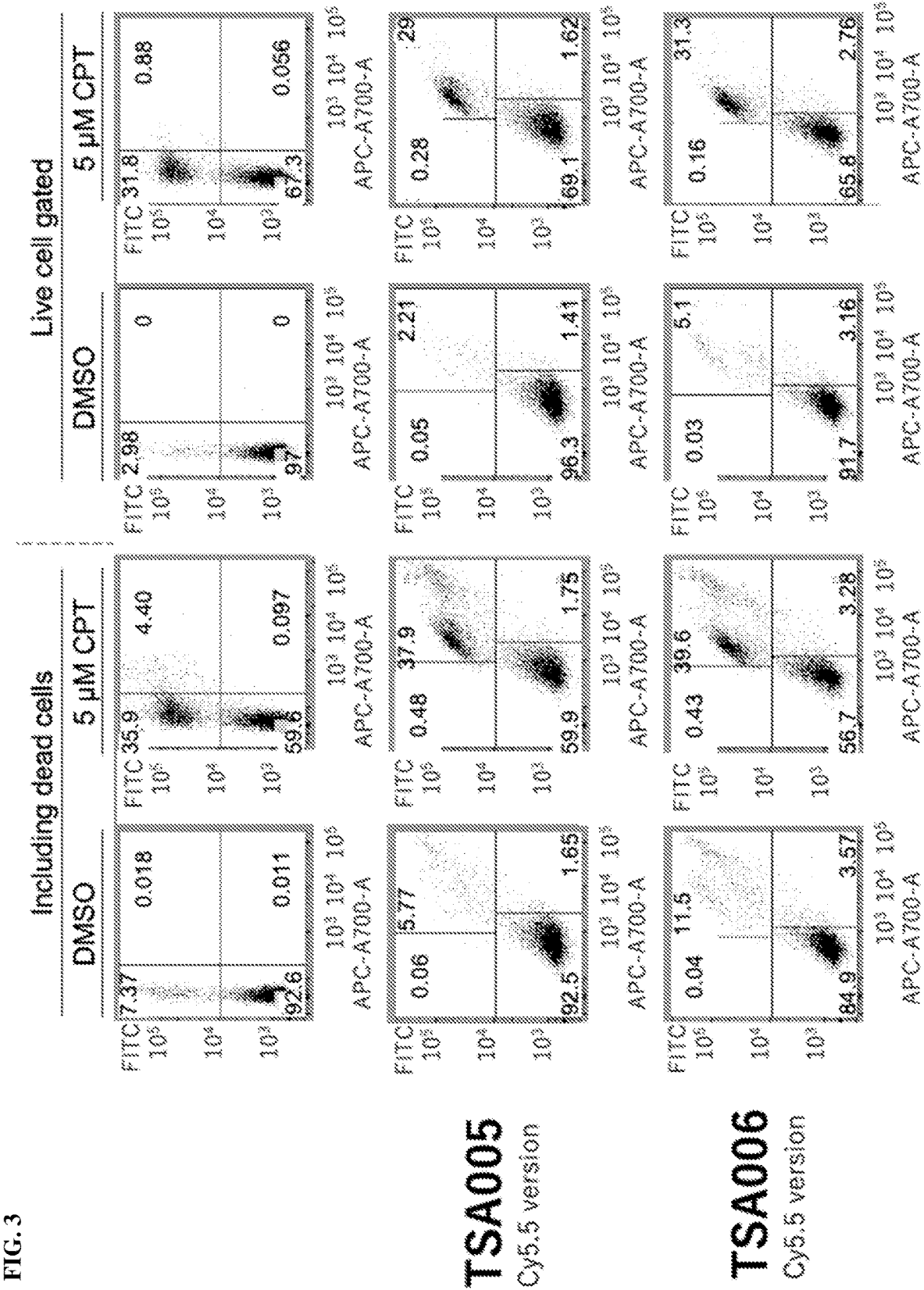
FIG. 3 presents flow-cytometry plots showing an exemplary analysis of a Cyanine-5.5 (Cy5.5) version of TSA005 and TSA006, stained with FITC-Annexin V. The data on the present figure shows double staining of Annexin V and TSA005 or TSA006.

Flow-Cytometry Analysis of Cy5.5 Version of TSA005 and 006 Stained with FITC-Annexin V (AnxV). (FIG. 3)

Cy5.5 (Cyanine-5.5) is a fluorescent compound with an excitation peak at 683 nm and an emission peak at 703 nm. Cy5.5 (Cyanine-5.5) is spectrally similar to TF6WS (Tide Fluor 6WS), Alexa Fluor 680, Alexa Fluor 700, and Rhodamine 800.

The Cy5.5 versions of TSA005 (TSA012) and TSA006 (TSA013) are dendrimers which CL264 in (TLVSSLr)4-K2-K-Cys(MI-CL264)-NH2 and (GEGKGGr)4-K2-K-Cys(MI-CL264)-NH2 were substituted by Cyanine5.5, respectively, and were synthesized at Peptide institute, Inc., Osaka, Japan. (MI: maleimide).

A human T cell line, Jurkat clone E6-1 (ATCC, TIB-152), was co-stained with Vehicle, TSA012 or TSA013 with FITC-AnxV (BioLegend, CA, 640906, lot #B345098) and analyzed by flow cytometry. Followings are brief experimental procedure.

To induce an apoptotic event, 5 µM camptothecin (Sigma, MO, C-9111) was added to 8×10⁵ Jurkat clone E6-1 cells in a T-75 flask and incubated for four hours. After washing cells with 10 mL of PBS(−) and AnxV binding buffer once each, 4×10⁵ cells were re-suspended in 100 µL of AnxV Binding Buffer in a 1.5 mL tube. Cells were incubated with 5 µL of diluted FITC-AnxV, TSA012, or TSA013 for 15 min at room temperature in the dark. Then, 10 µL of 20 µg/mL propidium iodide (final conc. 1.7 µg/mL) was added and incubated for 2 min on ice in the dark. 300 µL of AnxV binding buffer was added to each tube before analysis with a CytoFLEX (Beckman Coulter, IND). Acquired data were analyzed by FlowJo software.

Tumor Growth Curves of the Subcutaneously Implanted CT-26 Mouse Colon Cancer Cell Line in Syngeneic BALB/c Mice. (FIGS. 4A-4D)

BALB/c mice were implanted subcutaneously with 5×10⁵ cells mice colon cancer cell line, CT-26WT, at day −10 when the mice were at the age 6 weeks. Six mice made a group for each treatment when the average tumor size was 205 mm³ (132-279 mm³). Treatments were done as follows when the mice were at the age 8 weeks with body weight 19.5 to 24.5 g and tumor size were measured three times in a week.

Dosing schedule ("ip": intraperitoneal injection; "iv": intravenous injection):
  Diphenhydramine (ip): 10 mg/kg (15 min before Cisplatin/CBP501 on day 1)
  Cisplatin (iv): 4 mg/kg (day 1)
  CBP501 (iv): 6 mg/kg (day 1)

Figure 5:
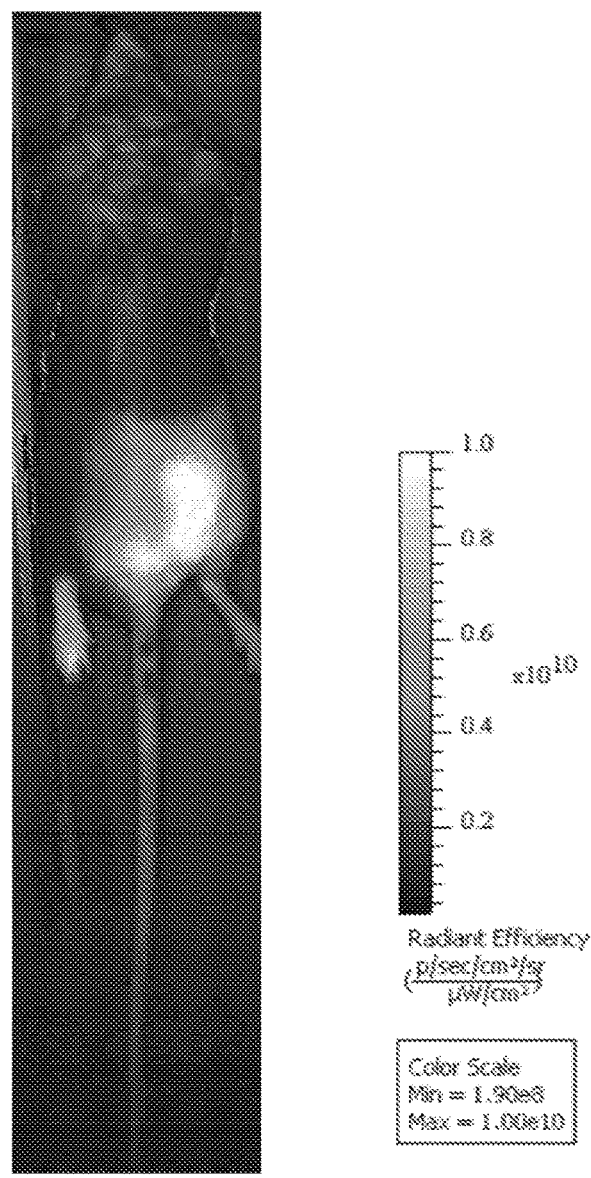
FIG. 5 shows the distribution of the Cy5.5 version of TSA006 (TSA013) after treatment of syngeneic BALB/c mice subcutaneously implanted the CT26 mouse colon cancer cell line with cisplatin, CBP501 and TSA013.

Anti-CTLA4 antibody (ip) 200 µg/mouse (day2, 4)
TSA005,006 in saline (iv): 100 µg/mouse (day 2×2, day3×1)
TSA015 in HEPES (iv): 100 µg/mouse (day 2×2, day3×1)
Vehicle: saline (iv): 100 µL/mouse (day 2×2, day3×1)
Distribution of the Cy5.5 Version of TSA006 (TSA013) in BALB/c Mouse. (FIG. 5)

Female BALB/c mice at 7 weeks of age were implanted with CT-26WT subcutaneously with 5×10$^5$ cells/mouse, and let the tumor grow to 114-190 mm$^3$ (average size:152 mm$^3$). After following treatment when the mice were at the age 9 weeks with body weight 23.0 to 24.0 g, the emitted lights from Cy5.5 were detected by IVIS LuminaX5 (Filter: Ex:660, Em:710) on day 4.

Treatments were as follows:
Diphenhydramine (ip): 10 mg/kg (15 min before cisplatin/CBP501 on day 1)
Cisplatin (iv): 4 mg/kg (on day 1)
CBP501 (iv): 6 mg/kg (on day 1)
TSA013 in saline (iv): 100 µg/mouse (on day 3)

Results

As shown in FIG. 1, the CBP501+cisplatin combination suppressed subcutaneous tumor growth much better than cisplatin alone. The addition of TSA005 to the combination further suppressed the tumor growth.

The addition of one of the immune checkpoint inhibitors, anti-CTLA4 antibody, suppressed the tumor growth for longer duration than the CBP501+cisplatin combination alone even though the three-drug combination with anti-CTLA4 was dosed for only one cycle of treatment compared to two cycles of treatments for the two-drug CBP501+cisplatin combination.

TSA005 enhanced anti-tumor activity when it was used in combination with either the two-drug or three-drug treatment regimen.

As shown in FIG. 2, the addition of TSA005, but not TSA009, suppressed CT26 subcutanous tumor growth more than just CBP501+cisplatin+anti-CTLA4 antibody an syngeneic tumor model.

Structure of TSA005: (TLVSSLr)4-K2-K-Cys(MI-CL264)-NH2.
Structure of TSA009: (TLVSSLr)8-K4-K2-K-Cys(MI-CL264)-NH2.

With regard to FIG. 2, a deleterious effect of TSA009 was observed when compared to the administration of CBP501+cisplatin+anti-CTLA4 antibody, with or without TSA005. One hypothesis for this observed effect of TSA009 could be that this conjugate acted as if it were delivered systematically but not to the apoptotic and/or cancerous cells.

As shown in FIG. 3, AnxV and TSA012 or TSA013 double positive cells in the upper right quadrant increased from 5.77 to 37.9 and 11.5 to 39.6% with Cy5.5 version of TSA005 (TSA012) and Cy5.5 version of TSA006 (TSA013), respectively, by the treatment of camptothecin which is known inducer of apoptosis to Jurkat cells. The highly double positive signals are likely come from dead cells because, as shown in the right 6 panels, the highly double positive signals were disappeared by gating only to live cells. Still, the AnxV and TSA012 or TSA013 double positive cells clearly increased by the treatment with camptothecin, e.g., 2.21 to 29% and 5.1 to 31.3%, respectively. This data presented in FIG. 3 suggested that TSA012 and TSA013 bound to AnxV binding cells. These cells were known to be apoptotic or dead cells.

Figure 4A:
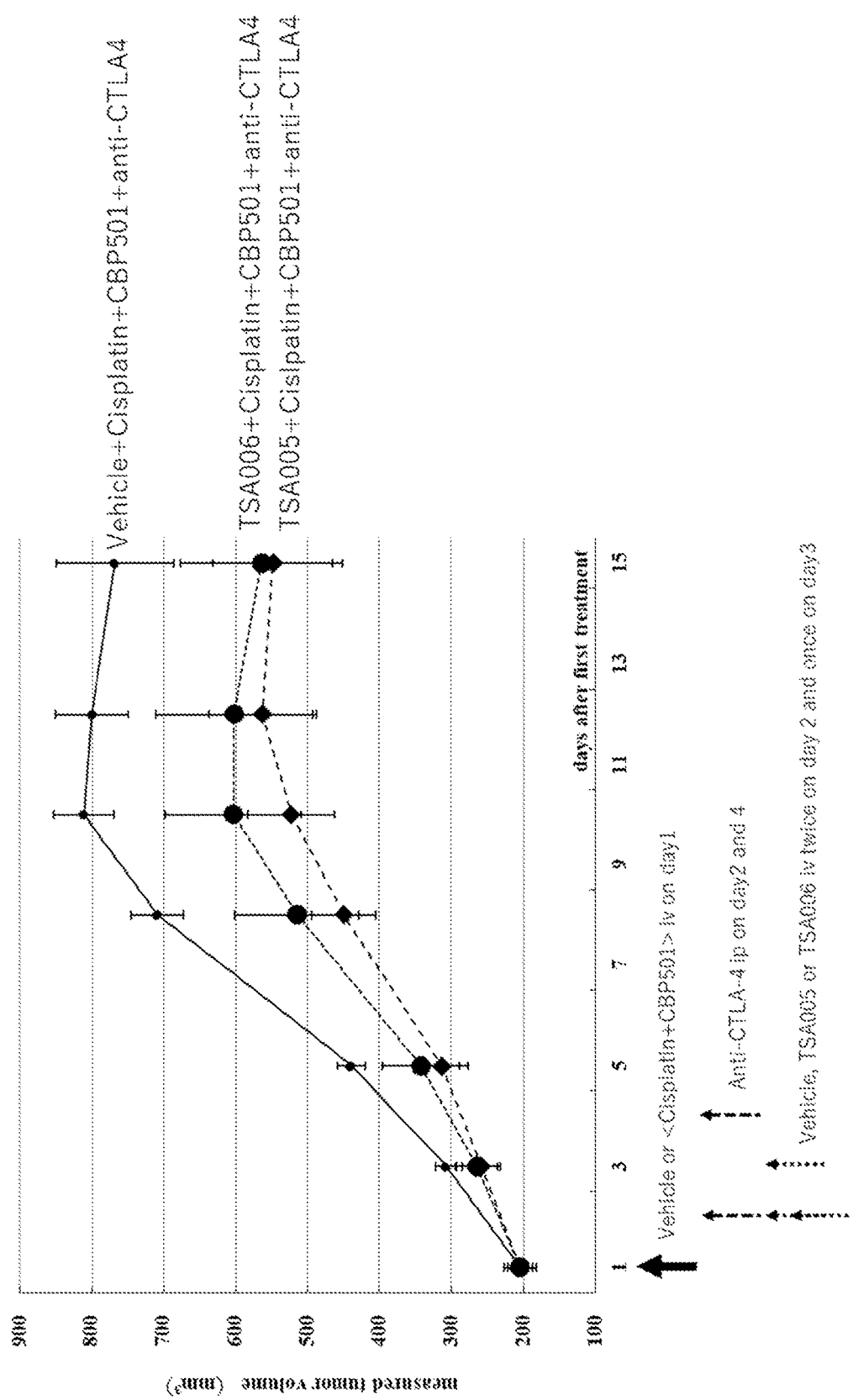
FIGS. 4A-4D presents the exemplary effects of TSA005 or TSA006 on subcutaneously implanted CT-26 mouse colon cancer cell line in syngeneic BALB/c mice.

The data presented in FIG. 4A shows that the CT26 tumor growth was suppressed by the treatment with Cisplatin, CBP501 and anti-CTLA-4 compared to vehicle, each single compound or each double combination (data not shown). The addition of TSA005 and TSA006 further suppressed the tumor growth. The addition of these compounds did not change the mouse body weight further than the triple drug combination (data not shown).

Figure 4B:
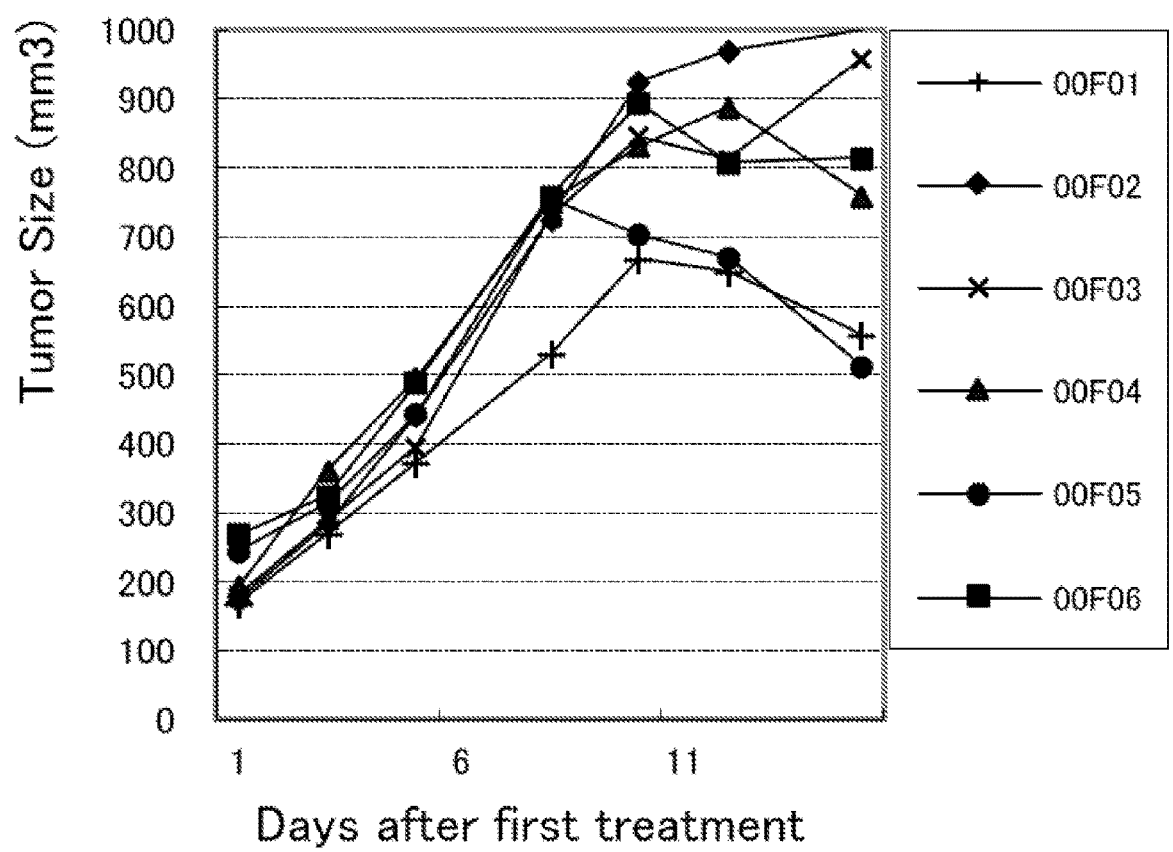
Figure 4C:
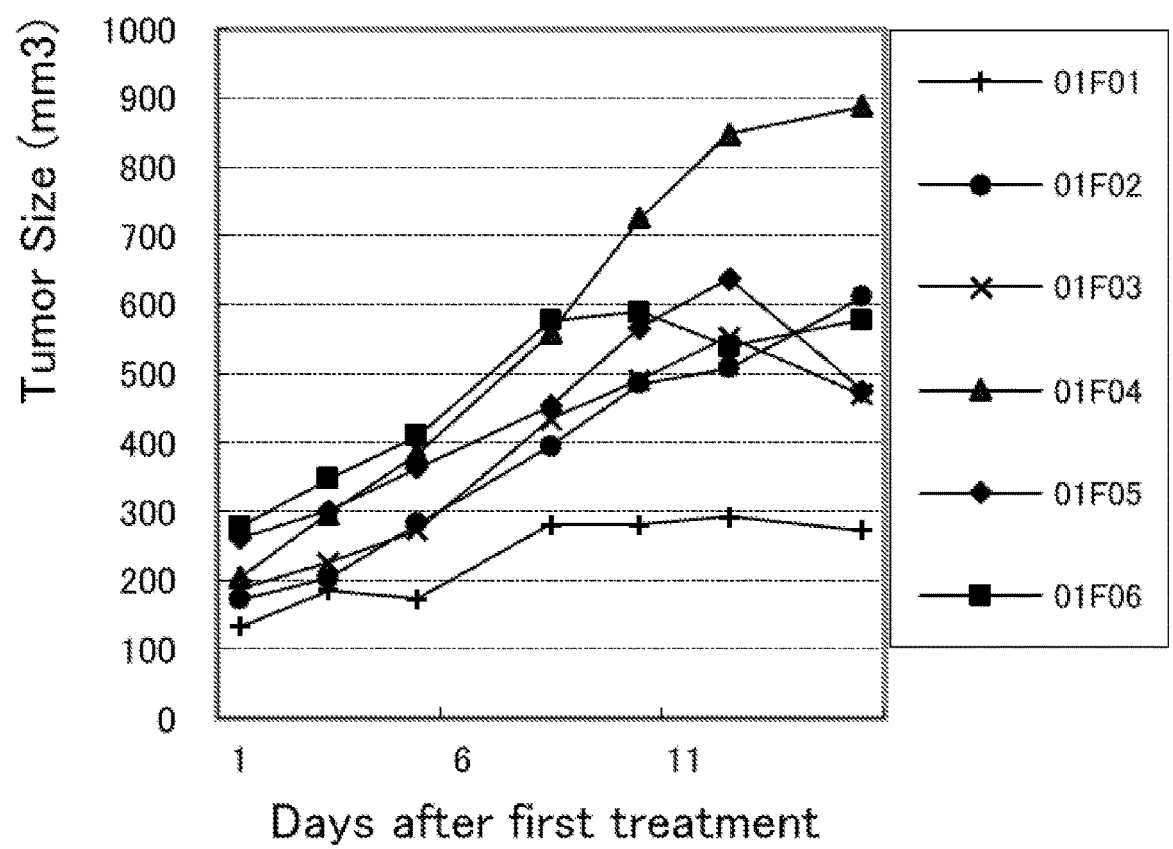
Figure 4D:
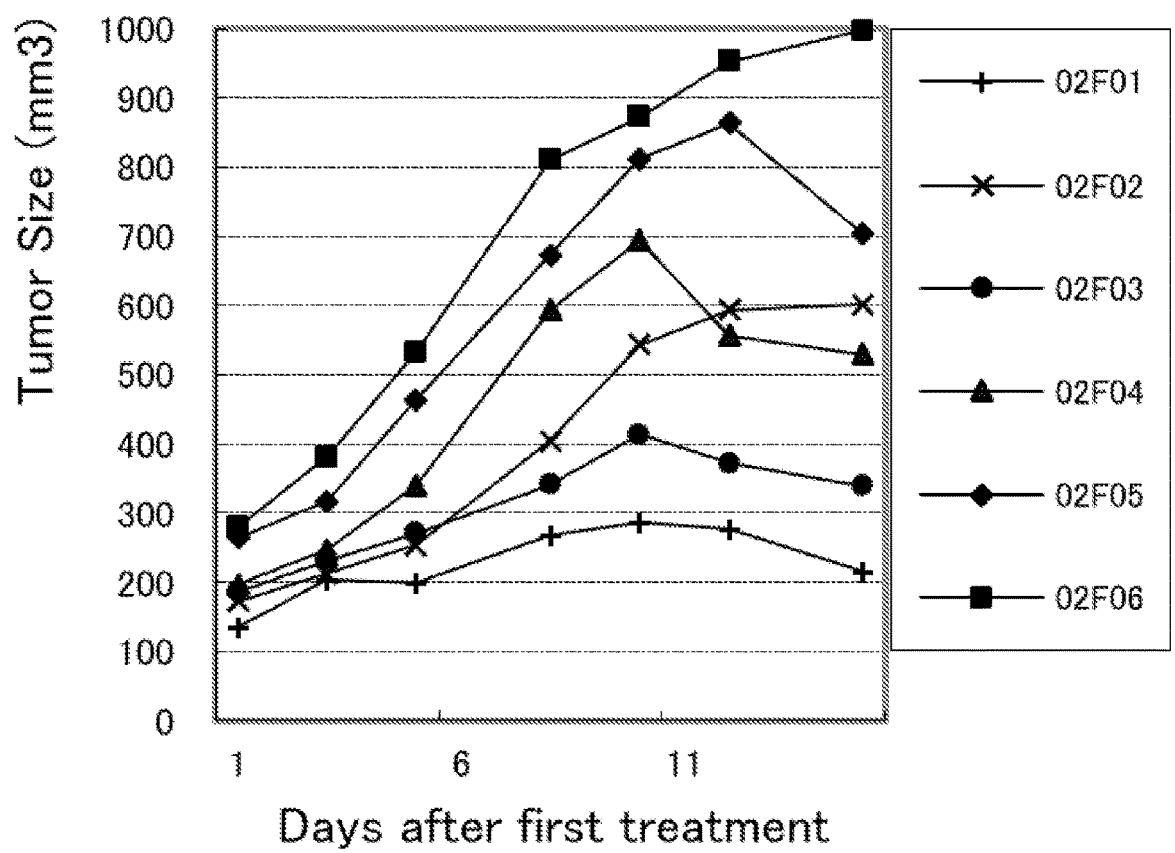

The data presented in FIGS. 4B-4D shows that unlike many cytotoxics, immune acting agents variably suppressed tumor growth even with the same treatment condition. The data also indicated that the smaller tumors tended to see their growth suppressed more than the larger tumors. The data was in-line with the expected immune related mechanism of action of TSA005 and TSA006.

The data presented in FIG. 5 shows that TSA013 accumulated to the implanted tumor sites where apoptosis was induced by the treatment of Cisplatin and CBP501.

Discussion

We have shown that CBP501 would increase the effect of platinum therapeutics in cancer cells (15, 16) and induce immunogenic cell death (17). CBP501 also suppresses cytokine release by macrophages and reduce accumulation of cancer stem cells (18). As expected, CBP501+Cisplatin suppressed tumor growth better than Cisplatin alone, and the addition of TSA005 further reduced the growth of the tumor.

Similarly, TSA005 reduced tumor growth further than the triple drug combination of CBP501+Cisplatin+anti-CTLA-4 antibody.

The data suggested that TSA005 is acting through different mechanism from the mechanisms of Cisplatin, CBP501 and anti-CTLA-4. As TSA005 includes phosphatidylserine binding and toll-like receptor agonist portions, we expect that it would be phagocytosed by the phagocytic cells together with the apoptotic cells and the phagocytosed toll-like receptor agonist portion would change the way of antigen presentation by the phagocytic cells from negative to positive way.

REFERENCES

1. J. A. Marin-Acevedol et al., Next generation of immune checkpoint inhibitors and beyond. J. Hematol. Oncol., 2021
2. A. D. Waldman et al., A guide to cancer immunotherapy: from T cell basic science to clinical practice. Nat. Rev. Imm., 2020
3. S. Pahlavanneshan et al., Toll-Like Receptor-Based Strategies for Cancer Immunotherapy. J. Imm. Res., 2021
4. A. Keshavarzl et al., Toll-like receptors (TLRs) in cancer; with an extensive focus on TLR agonists and antagonists. IUBMB Life. 2021
5. A. J. R. Gadd et al., Targeted Activation of Toll-Like Receptors: Conjugation of a Toll-Like Receptor 7 Agonist to a Monoclonal Antibody Maintains Antigen Binding and Specificity. Bioconjug Chem, 2015
6. S. E. Ackerman et al., Immune-stimulating antibody conjugates elicit robust myeloid activation and durable antitumor immunity. Nat. Can., 2020
7. G. M. Thurber et al., Antibody tumor penetration: Transport opposed by systemic and antigen-mediated clearance. Adv. Drug Deliv. Rev., 2008
8. W. Chang et al., Targeting phosphatidylserine for Cancer therapy: prospects and challenges. Theranostics, 2020
9. C. Burtea et al., Peptidic Targeting of Phosphatidylserine for the MRI Detection of Apoptosis in Atherosclerotic Plaques. Mol. Pharm., 2009
10. J. Kapty et al., Evaluation of Phosphatidylserine-Binding Peptides Targeting Apoptotic Cells. J. Bio. Scr., 2012

11. A. Perreault et al., Targeting Phosphatidylserine with a 64Cu-Labeled Peptide for Molecular Imaging of Apoptosis. Mol. Pharm., 2016
12. K. Igarashi et al., A Novel Phosphatidylserine-binding Peptide Motif Defined by an Anti-idiotypic Monoclonal Antibody. J.B.C., 1995
13. C. Laumonier et al., A New Peptidic Vector for Molecular Imaging of Apoptosis, Identified by Phage Display Technology. J. Bio. Scr., 2006
14. N. Thapa et al., Discovery of a phosphatidylserine-recognizing peptide and its utility in molecular imaging of tumour apoptosis. J. Cell. Mol. Med., 2008
15. S. Sha et al., Cell cycle phenotype-based optimization of G2 abrogating peptides yields CBP501 with a unique mechanism of action at the G2 checkpoint. Mol. Cancer Ther.,
16. N. Mine et al., CBP501-calmodulin binding contributes to sensitizing tumor cells to CDDP and BLM. Mol. Cancer Ther., 2011
17. K. Sakakibara et al., CBP501 induces immunogenic tumor cell death and CD8 T cell infiltration into tumors in combination with platinum, and increases the efficacy of immune checkpoint inhibitors against tumors in mice. Oncotarget, 2017
18. N. Mine et al., CBP501 suppresses macrophage induced cancer stem cell like features and metastases. Oncotarget, 2017
19. Barth et al., A fluorogenic cyclic peptide for imaging and quantification of drug-induced apoptosis. Nature Communications vol 11: 4027, 2020

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

Some embodiments of the technology described herein suitably can be practiced in the absence of an element not specifically disclosed herein. Accordingly, in some embodiments the term "comprising" or "comprises" can be replaced with "consisting essentially of" or "consisting of" or grammatical variations thereof. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

We claim:

1. A phosphatidylserine-binding (PS-binding) conjugate, wherein the conjugate comprises more than two PS-binding peptide sequences selected from the group consisting of: LIKKPF (SEQ ID NO:1), PGDLSR (SEQ ID NO: 2), CLIKKPF (SEQ ID NO:3), CPGDLSR (SEQ ID NO:4), FNFRLKAGAKIRFG (SEQ ID NO:5), FXFXLKXXXKXR (SEQ ID NO:6), TLVSSL (SEQ ID NO:7), CLSYYPSYC (SEQ ID NO:8), GEGKGGr (SEQ ID NO:9), gegkggr (SEQ ID NO:10), GEGr (SEQ ID NO:11), gegr (SEQ ID NO:12), GE, ge, RGEGR (SEQ ID NO:13), rgegr (SEQ ID NO:14), and Cyclo(RKKWFGC) (SEQ ID NO:15); wherein a capital letter indicates a L-amino acid, and a non-capitalized letter indicates a D-amino acid, and wherein "X" represents any L-amino acid, and at least one Toll-like Receptor binding (TLR-binding) domain.

2. The conjugate of claim 1, wherein the TLR-binding domain is a TLR agonist.

3. The conjugate of claim 1, wherein one of the PS-binding peptide sequences is GEGKGGr (SEQ ID NO:9).

4. The conjugate of claim 3, wherein the conjugate comprises a tetramer of GEGKGGr (SEQ ID NO:9).

5. The conjugate of claim 2, wherein the TLR agonist is selected from the group consisting of: Pam3Cys, PAM3CSK4, PAM3CSK4, SMP-105, CBLB612, IPH 3102, ARNAX, MPLA, MALP-2, Zymosan, Poly (I:C), Poly-ICLC, Poly-IC12U, GLA-SE, BNT411, AS04, AS15, OK-432, CBLB502, M-VM3, Bistriazolyl, VTX1463, MGN1703, CpG-7909, IMO2055, dSLIM, SD-101, KSK-CpG, ODN M362, CpG-1826, LPS, Flagellin, Imiquimod, Motolimod, Rintatolimod, CL264, Imidazoquinoline, Resiquimod, Tilsotolimod, UC-1V150, CADI-05, GNKG168, RO7119929, SHR2150, CMP-001, and CpG ODN.

6. The conjugate of claim 5, wherein the TLR agonist is CL264.

7. The conjugate of claim 4, wherein the TLR-binding domain is the TLR agonist CL264.

8. The conjugate of claim 1 further comprises a linker moiety linking the more than two PS-binding peptide sequences to the TLR-binding domain.

9. A method of treating a subject with cancer comprising administering the conjugate of claim 1 to the subject.

10. The method of claim 9, wherein the cancer is a solid cancer or a solid tumor.

11. The method of claim 9, wherein the cancer is a blood-based cancer.

12. The method of claim 9, wherein the cancer is colon cancer.

13. The method of claim 11, wherein the cancer is leukemia.

14. The method of claim 9, wherein the subject is human.

15. The method of claim 9, wherein the method further comprises administering to the subject an anti-cancer agent, and/or an immunologic agent.

16. The method of claim 15, wherein the anti-cancer agent is a serine/threonine kinase inhibitor.

17. The method of claim 16, wherein the serine/threonine kinase inhibitor is a peptide compound comprising (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) (SEQ ID NO:16).

18. The method of claim 15, wherein the immunologic agent is an antibody.

19. The method of claim 18, wherein the antibody is an anti-CTLA-4, anti-PD1, anti-PD-L1, anti-PDL2, anti-VISTA, anti-TIM3, anti-LAG-3 or anti-BTLA antibody.

20. The method of claim 19, wherein the antibody is an anti-CTLA-4 antibody.

21. The method of claim 15, wherein the method further comprises administering a platinum-containing drug.

22. The method of claim 21, wherein the platinum-containing drug is cisplatin.

* * * * *